United States Patent
Liu et al.

(10) Patent No.: US 10,071,139 B2
(45) Date of Patent: Sep. 11, 2018

(54) METHODS FOR TREATMENT OF CONDITIONS ASSOCIATED WITH ELEVATED TRIGLYCERIDES WITH AN ANGPTL8 POLYPEPTIDE FRAGMENT

(71) Applicant: NGM Biopharmaceuticals, Inc., South San Francisco, CA (US)

(72) Inventors: Zhonghao Liu, San Bruno, CA (US); Xunshan Ding, San Bruno, CA (US)

(73) Assignee: NGM Biopharmaceuticals, Inc., South San Francisco, CA (US)

(*) Notice: Subject to any disclaimer, the term of this patent is extended or adjusted under 35 U.S.C. 154(b) by 0 days.

(21) Appl. No.: 15/318,937

(22) PCT Filed: Oct. 2, 2015

(86) PCT No.: PCT/US2015/053700
§ 371 (c)(1),
(2) Date: Dec. 14, 2016

(87) PCT Pub. No.: WO2016/054494
PCT Pub. Date: Apr. 7, 2016

(65) Prior Publication Data
US 2017/0143799 A1    May 25, 2017

Related U.S. Application Data

(60) Provisional application No. 62/059,682, filed on Oct. 3, 2014.

(51) Int. Cl.
*A61P 3/06* (2006.01)
*A61K 38/22* (2006.01)
*C07K 14/575* (2006.01)
*G01N 33/92* (2006.01)

(52) U.S. Cl.
CPC ........... *A61K 38/22* (2013.01); *A61P 3/06* (2018.01); *C07K 14/575* (2013.01); *G01N 33/92* (2013.01); *C07K 2319/00* (2013.01); *C07K 2319/30* (2013.01); *C07K 2319/31* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 2014/0179596 A1 | 6/2014 | Rosen et al. | |
| 2014/0303078 A1* | 10/2014 | Melton | A61K 48/005 514/6.7 |

FOREIGN PATENT DOCUMENTS

| | | |
|---|---|---|
| WO | 2012170977 | 12/2012 |
| WO | 2014110368 | 7/2014 |

OTHER PUBLICATIONS

Yi et al (2013. Cell. 153: 747-758).*
Yi et al (2017. Cell. 168(1-2): 326).*
Wang et al (2013. PNAS. 110(40): 16109-16114).*
Gusarova et al (2014. 159(3):691-696).*
Santulli, Gaetano, (2014) "Angiopoietin-like proteins: a comprehensive look", frontiers in Endocrinology, 5(4):1-6.

* cited by examiner

*Primary Examiner* — Zachary C Howard
(74) *Attorney, Agent, or Firm* — Shweta Chandra; Bozicevic, Field & Francis LLP

(57) ABSTRACT

Methods and compositions for reducing one or more of triglyceride levels, total cholesterol levels and LDL cholesterol levels in a subject are provided. The methods include administering a fragment of ANGPTL8 to a subject having or at risk of developing elevated triglyceride levels, elevated total cholesterol levels and/or elevated LDL cholesterol levels.

20 Claims, 4 Drawing Sheets

Specification includes a Sequence Listing.

METHODS FOR TREATMENT OF CONDITIONS ASSOCIATED WITH ELEVATED TRIGLYCERIDES WITH AN ANGPTL8 POLYPEPTIDE FRAGMENT

CROSS REFERENCE TO RELATED APPLICATIONS

This application claims priority benefit of U.S. provisional application Ser. No. 62/059,682, filed on Oct. 3, 2014, which application is incorporated herein by reference in its entirety.

INCORPORATION BY REFERENCE OF SEQUENCE LISTING PROVIDED AS A TEXT FILE

A Sequence Listing is provided herewith as a text file, "NGMB-137_SeqList.txt" created on Oct. 1, 2015 and having a size of 25 KB. The contents of the text file are incorporated by reference herein in their entirety.

INTRODUCTION

According to the American Heart Association, it is estimated that about one-third of United States adults have elevated triglyceride levels greater than 150 milligrams per deciliter (mg/dl) (Miller et al. (2011) *Circulation.* 123:2292-2333). From a sample of subjects from the National Health and Nutrition Examination Survey, it is further estimated that an average of 1.7% of the national population had severe hypertriglyceridemia (characterized as 500 to 2,000 mg/dl) between 2001 and 2006 (Christian et al. (2011) *Am J Cardiol.* 107(6):891-7).

Elevated blood triglyceride levels and hypertriglyceridemia are significant contributing factors to increased risk of heart disease, heart attack, stroke, and atherosclerosis. Elevated triglyceride levels can also be a sign of and contributing factor to adverse conditions that increase a person's overall risk of heart disease, such as obesity, metabolic syndrome, excess body fat, high blood pressure, high blood sugar, and abnormal cholesterol levels. In addition high triglyceride levels contribute to further decline in health of subjects with poorly controlled type 2 diabetes, hypothyroidism, liver disease, kidney disease, and genetic metabolic disorders. Further complicating treatment for associated conditions, elevated triglyceride levels are a common side effect of routinely prescribed medications such as beta blockers, birth control, diuretics, steroids, and certain cancer treatments, such as tamoxifen.

Accordingly, reducing triglyceride levels, particularly reducing elevated triglyceride levels into normal ranges can have a significant impact on a subject's health and well-being. Reducing triglyceride levels is associated with a decreased risk of heart disease, heart attack, stroke, and atherosclerosis. Furthermore, maintaining normal triglyceride levels is associated with effective management of obesity, metabolic syndromes, high blood pressure, abnormal cholesterol, diabetes, hyperthyroidism, liver disease, kidney disease, and genetic metabolic disorders. In addition, lowering triglyceride levels and/or preventing their increase may allow a subject to begin or continue a course of treatment that may otherwise adversely increase triglyceride levels, for example, treatments with drugs known to increase triglyceride levels including beta blockers, birth control, diuretics, steroids, and certain cancer treatments, such as tamoxifen.

Lifestyle changes, such as reducing dietary triglyceride or cholesterol intake and increasing exercise, can reduce elevated triglyceride or cholesterol levels. However, lifestyle changes are not effective for all patients. Some patients are not physically capable of making certain lifestyle changes, such as increasing exercise, because of other complicating health factors. Furthermore, lifestyle change regimens, such as exercise programs and dieting, are often subject to poor patient adherence which may result in elevated triglyceride and/or cholesterol levels over time. Pharmacologically reducing triglyceride and/or cholesterol levels in subjects that are incapable to initially make healthy lifestyle changes not only provides the direct benefits of reduced triglyceride levels, but may also increase the patient's condition to a state such that certain lifestyle changes may be initiated. Likewise, pharmacological reduction of triglyceride and/or cholesterol levels in subjects capable of but unwilling to make or maintain certain lifestyle changes may also provide the initial incentive to start or adhere to such lifestyle changes as, e.g., exercise regimens and healthy eating habits.

SUMMARY

Methods and compositions for reducing triglyceride levels in a subject are provided. The methods include administering a fragment of ANGPTL8 to a subject having or at risk of developing elevated triglyceride levels.

In certain embodiments, a method for reducing triglyceride levels in a subject having or at risk of developing elevated triglyceride levels is provided. The method may include administering to the subject a polypeptide comprising a contiguous amino acid sequence having at least 85% sequence identity (e.g., at least 90%, at least 93%, at least 95%, at least 98%, at least 99%, or 100% sequence identity) to the amino acid sequence of amino acids 80-198 of full-length ANGPTL8 (SEQ ID NO. 1), where the polypeptide lacks the amino acids 21-74 of full-length ANGPTL8 (SEQ ID NO: 1), and where the polypeptide is administered in an amount effective to reduce the triglyceride levels in the subject.

In certain embodiments, the contiguous amino acid sequence may have at least 90% sequence identity to the amino acid sequence of amino acids 80-198 of full-length ANGPTL8 (SEQ ID NO. 1).

In certain embodiments, the contiguous amino acid sequence has at least 95% sequence identity to the amino acid sequence of amino acids 80-198 of full-length ANGPTL8 (SEQ ID NO. 1).

In certain embodiments, a heterologous polypeptide may be conjugated to the N-terminus or C-terminus of the polypeptide. The heterologous polypeptide may be albumin, such as human serum albumin, or immunoglobulin Fc. The heterologous polypeptide may be conjugated to the polypeptide via a linker sequence. In certain cases, the linker sequence may be a cleavable linker sequence. In other instances, the linker sequence may be a non-cleavable linker sequence.

In exemplary methods, the administering may reduce triglyceride levels by at least 10% compared to triglyceride levels in the subject prior to the administering of the polypeptide. For example, the administering may reduce triglyceride levels by at least 20% or 30% compared to triglyceride levels in the subject prior to the administering of the polypeptide.

The subject may be overweight, obese, may have diabetes, cardiovascular disease, hypothyroidism, or a combination thereof.

Methods and compositions for reducing total cholesterol and LDL cholesterol levels in a subject are provided. The methods include administering a fragment of ANGPTL8 to a subject having or at risk of developing elevated total cholesterol or LDL cholesterol.

In certain embodiments, a method of reducing total cholesterol levels in a subject having or at risk of developing elevated total cholesterol levels is disclosed. The method includes administering to the subject a polypeptide that includes a contiguous amino acid sequence having at least 85% sequence identity (e.g., at least 90%, at least 93%, at least 95%, at least 98%, at least 99%, or 100% sequence identity) to the amino acid sequence of amino acids 80-198 of full-length ANGPTL8 (SEQ ID NO. 1), where the polypeptide lacks the amino acids 21-70 of full-length ANGPTL8 (SEQ ID NO: 1), and where the polypeptide is administered in an amount effective to reduce the total cholesterol levels in the subject.

In certain embodiments, the administering may reduces total cholesterol levels by at least 5%, 10%, 20%, or more compared to total cholesterol levels in the subject prior to the administering of the polypeptide.

A method of reducing low-density lipoprotein (LDL) cholesterol levels in a subject having or at risk of developing elevated LDL cholesterol levels is also disclosed. The method may include administering to the subject a polypeptide that includes a contiguous amino acid sequence having at least 85% sequence identity (e.g., at least 90%, at least 93%, at least 95%, at least 98%, at least 99%, or 100% sequence identity) to the amino acid sequence of amino acids 80-198 of full-length ANGPTL8 (SEQ ID NO. 1), where the polypeptide lacks the amino acids 21-70 of full-length ANGPTL8 (SEQ ID NO: 1), and where the polypeptide is administered in an amount effective to reduce the LDL cholesterol levels in the subject.

In exemplary embodiments, the administering may reduce LDL cholesterol levels by at least 5%, 10%, 15%, or more compared to LDL cholesterol levels in the subject prior to the administering of the polypeptide.

The contiguous amino acid sequence of the polypeptide may have at least 90%, at least 95%, 97%, 99%, or more sequence identity to the amino acid sequence of amino acids 80-198 of full-length ANGPTL8 (SEQ ID NO. 1).

A heterologous polypeptide may be conjugated to the N-terminus or C-terminus of the polypeptide in exemplary cases. The heterologous polypeptide is albumin, e.g., human serum albumin, or immunoglobulin Fc. The heterologous polypeptide may be conjugated to the polypeptide via a linker sequence, such as a cleavable or a non-cleavable linker sequence.

Exemplary subjects include a subject who is overweight, obese, has diabetes, has hypothyroidism, cardiovascular disease or a combination of these conditions.

BRIEF DESCRIPTION OF THE DRAWINGS

FIG. 2A. Construct design; FIG. 2B. Plasma triglyceride levels before overexpression; FIG. 2C. Plasma triglyceride levels after 2 weeks of overexpression by AAV.

DEFINITIONS

Figure 1:
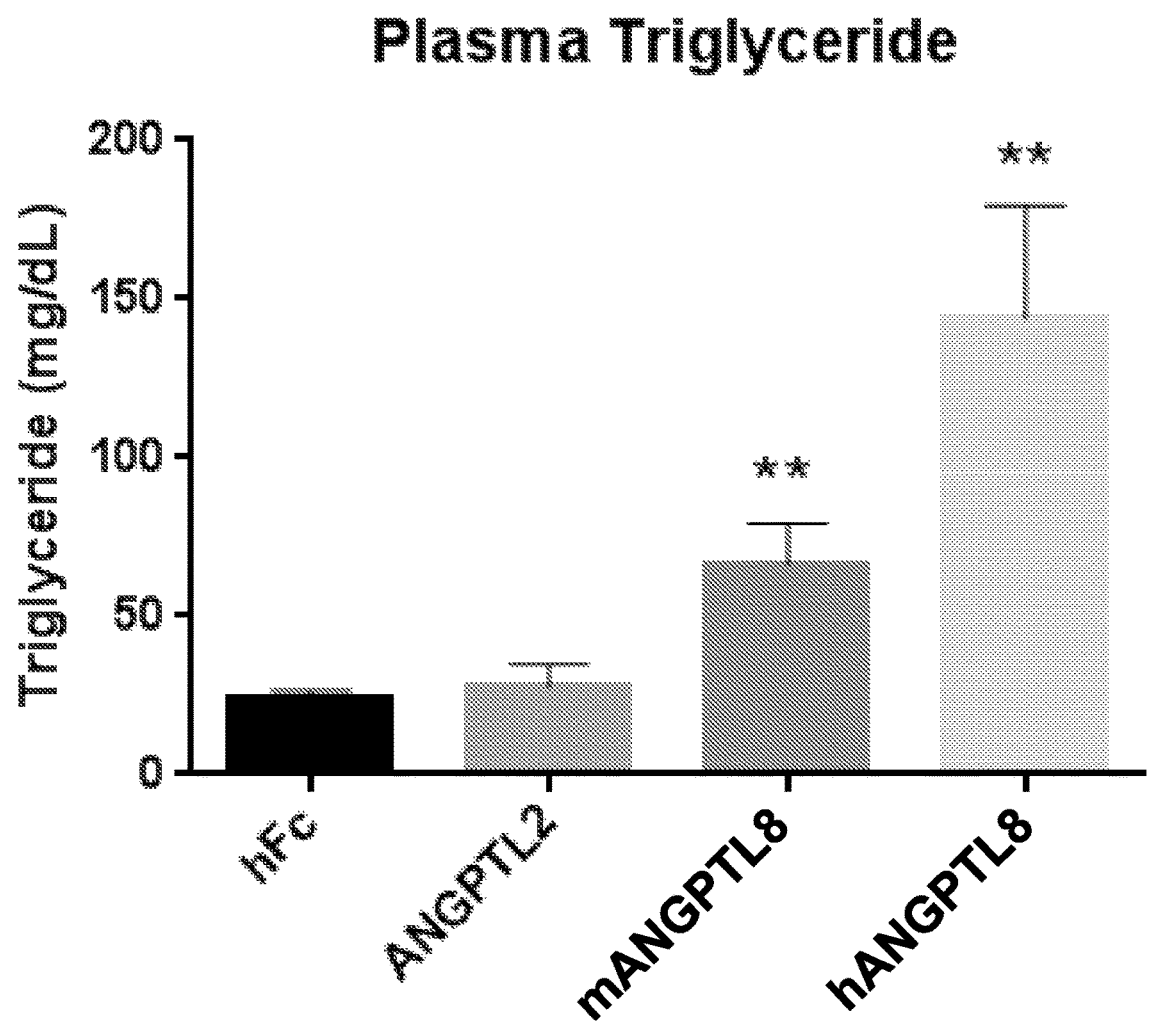
FIG. 1 indicates that overexpression of ANGPTL8 increased plasma triglyceride in mice.

The terms "patient" or "subject" as used interchangeably herein in the context of therapy, refer to a human and non-human animal, as the recipient of a therapy or preventive care.

The terms "treat", "treating", treatment" and the like refer to a course of action (such as administering an agent, e.g., a polypeptide or a pharmaceutical composition comprising a polypeptide) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (i.e., arresting the development or further development of the disease, disorder or condition or clinical symptoms associated therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an agent, e.g., a polypeptide or a pharmaceutical composition comprising a polypeptide) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects. The therapeutically effective amount can be adjusted in connection with the dosing regimen and diagnostic analysis of the subject's condition and the like.

The phrase "in a sufficient amount to effect a change" means that there is a detectable difference between a level of an indicator measured before (e.g., a baseline level) and after administration of a particular therapy.

As used herein, "homologues" or "variants" refers to protein or DNA sequences that are similar based on their amino acid or nucleic acid sequences, respectively. Homologues or variants encompass naturally occurring DNA sequences and proteins encoded thereby and their isoforms. The homologues also include known allelic or splice variants of a protein/gene. Homologues and variants also encompass nucleic acid sequences that vary in one or more bases from a naturally-occurring DNA sequence but still translate into an amino acid sequence that corresponds to the naturally-occurring protein due to degeneracy of the genetic code. Homologues and variants may also refer to those that differ from the naturally-occurring sequences by one or more conservative substitutions and/or tags and/or conjugates.

The terms "polypeptide" and "protein", used interchangeably herein, refer to a polymeric form of amino acids, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "nucleic acid molecule" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The term "heterologous" refers to two components that are defined by structures derived from different sources. For example, where "heterologous" is used in the context of a polypeptide, where the polypeptide includes operably linked amino acid sequences that can be derived from different polypeptides (e.g., a first component consisting of a tag peptide or protein and a second component derived from ANGPTL8 polypeptide). Similarly, "heterologous" in the context of a polynucleotide encoding a chimeric polypeptide includes operably linked nucleic acid sequences that can be derived from different genes (e.g., a first component from a nucleic acid encoding a peptide according to an embodiment disclosed herein and a second component from a nucleic acid encoding a carrier polypeptide). Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin relative to the promoter, the coding sequence or both). For example, a T7 promoter operably linked to a polynucleotide encoding a ANGPTL8 polypeptide or domain thereof is said to be a heterologous nucleic acid. "Heterologous" in the context of recombinant cells can refer to the presence of a nucleic acid (or gene product, such as a polypeptide) that is of a different genetic origin than the host cell in which it is present.

The term "operably linked" refers to functional linkage between molecules to provide a desired function. For example, "operably linked" in the context of nucleic acids refers to a functional linkage between nucleic acids to provide a desired function such as transcription, translation, and the like, e.g., a functional linkage between a nucleic acid expression control sequence (such as a promoter or array of transcription factor binding sites) and a second polynucleotide, wherein the expression control sequence affects transcription and/or translation of the second polynucleotide. "Operably linked" in the context of a polypeptide refers to a functional linkage between amino acid sequences (e.g., of different domains) to provide for a described activity of the polypeptide.

As used herein in the context of the structure of a polypeptide, "N-terminus" and "C-terminus" refer to the extreme amino and carboxyl ends of the polypeptide, respectively, while "N-terminal" and "C-terminal" refer to relative positions in the amino acid sequence of the polypeptide toward the N-terminus and the C-terminus, respectively, and can include the residues at the N-terminus and C-terminus, respectively.

"Derived from" in the context of an amino acid sequence or polynucleotide sequence (e.g., an amino acid sequence "derived from" a ANGPTL8 polypeptide) is meant to indicate that the polypeptide or nucleic acid has a sequence that is based on that of a reference polypeptide or nucleic acid (e.g., a naturally occurring ANGPTL8-encoding nucleic acid), and is not meant to be limiting as to the source or method in which the protein or nucleic acid is made.

"Isolated" refers to a protein of interest that, if naturally occurring, is in an environment different from that in which it may naturally occur. "Isolated" is meant to include proteins that are within samples that are substantially enriched for the protein of interest and/or in which the protein of interest is partially or substantially purified. Where the protein is not naturally occurring, "isolated" indicates the protein has been separated from an environment in which it was made by either synthetic or recombinant means.

"Enriched" means that a sample is non-naturally manipulated (e.g., by a scientist or a clinician) so that a protein of interest is present in a greater concentration (e.g., at least three-fold greater, at least 4-fold greater, at least 8-fold greater, at least 64-fold greater, or more) than the concentration of the protein in the starting sample, such as a biological sample (e.g., a sample in which the protein naturally occurs or in which it is present after administration), or in which the protein was made (e.g., as in a bacterial protein and the like).

"Substantially pure" indicates that an agent (e.g., polypeptide) makes up greater than about 50% of the total content of the composition (e.g., total protein of the composition) and typically, greater than about 60% of the total protein content. More typically, "substantially pure" refers to compositions in which at least 75%, at least 85%, at least 90% or more of the total composition is the agent of interest (e.g., 95% of the total protein). Preferably, the protein will make up greater than about 90%, and more preferably, greater than about 95% of the total protein in the composition.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a dose" includes a plurality of such doses and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Methods for reducing one or more of triglyceride levels, total cholesterol levels, and LDL cholesterol levels in a subject are provided. In certain embodiments, the methods include administering a polypeptide of the present disclosure, where the polypeptide is administered in an amount effective to reduce one or more of the triglyceride levels, total cholesterol levels, and LDL cholesterol levels in the subject.

The present disclosure provides the use of polypeptides encompassing fragments of an amino acid sequence of a ANGPTL8 polypeptide and homologues from different species, and use of such proteins in preparation of a formulation for therapy and in methods of reducing triglyceride levels in a patient. Exemplary embodiments of such are described below. The inventors have discovered that while administration of full length ANGPTL8 results in elevated triglyceride levels, a fragment of ANGPTL8 lacking an N-terminal region of the full length ANGPTL8 acts as a dominant negative by decreasing triglyceride levels. The fragment contains coiled-coiled domains present in the full length ANGPTL8.

The terms "betatrophin", "betatrophin variant 1", "betatrophin variant 2", "Angiopoietin-like protein 8", "Angptl8", "Angptl8", "Lipasin" and "hepatocellular carcinoma-associated protein TD26" are used interchangeably herein to describe the ANGPTL8 protein (Uniprot ID: UNQ599/PRO1185), expression products of the "ANGPTL8 gene", also known as "C19orf80", "hepatocellular carcinoma-associated gene TD26", "TD26", "PRO1185", "PVPA599" and "RIFL" (NCBI Gene ID:55908). ANGPTL8 encompasses human and murine variants that are encoded by the ANGPTL8 gene or a gene homologous to the ANGPTL8 gene.

The full length amino acid sequence of human ANGPTL8 is:

MPVPALCLLWALAMVTRPASAAPMGGPELAQHE ELTLLFHGTLQLGQA LNGVYRTTEGRLTKARNSLG-LYGRTIELLGQEVSRGRDAAQELRASLLETQMEED-ILQL QAEATAEVLGEVAQAQKVLRDSVQRLEVQLR-SAWLGPAYREFEVLKAHADKQSHILW ALTGHVQRQRREMVAQQHRLRQIQERLHTAALPA (SEQ ID NO: 1; predicted signal peptide is underlined). The consensus human genomic locus that encodes ANGPTL8 may be identified as C19orf80 or NC_018930.2 (SEQ ID NO: 2) which generates a corresponding mRNA represented by sequence NM_018687.6 (SEQ ID NO: 3).

In relationship to the human ANGPTL8 reference sequence set forth in SEQ ID NO: 1, human ANGPTL8 protein contains a signal peptide from residues 1-21 and a ANGPTL8 chain from resides 22-198 which contains two predicted coiled-coil domains from residues 76-140 and 165-194.

In some instances, a polypeptide for use in the methods disclosed herein may be a ANGPTL8 fragment that includes a contiguous amino acid sequence having at least 85% sequence identity to the amino acid sequence of ANGPTL8 (SEQ ID NO. 1), where the polypeptide lacks an N-terminal segment of ANGPTL8, where the N-terminal segment is at least 70 amino acids long.

In certain cases, the contiguous amino acid sequence may be up to 125 amino acids long and may have at least 85%, 90%, 95%, 98%, 99%, or 100% sequence identity to the amino acid sequence of ANGPTL8 (SEQ ID NO. 1), and lack the first 70 amino acids of the sequence of SEQ ID NO: 1. In other cases, this contiguous amino acid sequence may be up to 120, 119, 118, 115, 112, or 110 amino acids long and may have at least 85%, 90%, 95%, 98%, 99%, or 100% sequence identity to the amino acid sequence of ANGPTL8 (SEQ ID NO. 1), and lack the first 70 amino acids of the sequence of SEQ ID NO: 1.

In some instances, a polypeptide for use in the methods disclosed herein may be a polypeptide comprising a contiguous amino acid sequence having at least 85% sequence identity to the amino acid sequence of amino acids 80-198 of full-length ANGPTL8 (SEQ ID NO. 1), wherein the polypeptide lacks the amino acids 21-70 of full-length ANGPTL8 (SEQ ID NO: 1). In some embodiments, the polypeptide may include a contiguous amino acid sequence having at least 90%, 95%, 97%, 99%, or 100% sequence identity to the amino acid sequence of amino acids 80-198 of full-length ANGPTL8 (SEQ ID NO. 1), wherein the polypeptide lacks the amino acids 21-74 of full-length ANGPTL8 (SEQ ID NO: 1).

In some embodiments, the polypeptide may include a contiguous amino acid sequence having at least 85%, 90%, 95%, 97%, 99%, or 100% sequence identity to the amino acid sequence of amino acids 80-198 of full-length ANGPTL8 (SEQ ID NO. 1), wherein the polypeptide lacks the amino acids 21-75, 21-76, 21-77, 21-78, 21-79, 21-80, or 21-85 of full-length ANGPTL8 of SEQ ID NO: 1 and where the contiguous amino acid sequence is 118-121, 119-121, 120-121, 121, 117-118, 117-119, 117-120, 118-125, 118-130, 119-135, or 119-140 amino acids long, such as 140, 130, 120, 122, 121, 117, 119, or 110 amino acids long.

In certain cases, the polypeptide may include a contiguous amino acid sequence having at least 85%, 90%, 95%, 97%, 99%, or 100% sequence identity to the amino acid sequence of amino acids 76-140 of full-length ANGPTL8 (SEQ ID NO. 1).

In certain cases, the polypeptide may include a contiguous amino acid sequence having at least 85%, 90%, 95%, 97%, 99%, or 100% sequence identity to the amino acid sequence of amino acids 165-194 of full-length ANGPTL8 (SEQ ID NO. 1).

In certain cases, the polypeptide may include a contiguous amino acid sequence that includes a first contiguous amino acid sequence operably linked to a second contiguous amino acid sequence, where the first contiguous amino acid sequence has at least 85%, 90%, 95%, 97%, 99%, or 100% sequence identity to the amino acid sequence of amino acids 76-140 of full-length ANGPTL8 (SEQ ID NO. 1) and the second contiguous amino acid sequence has at least 85%, 90%, 95%, 97%, 99%, or 100% sequence identity to the amino acid sequence of amino acids 165-194 of full-length ANGPTL8 (SEQ ID NO. 1). In certain embodiments, the first and second contiguous amino acid sequences may be joined via an intervening sequence, such as a linker sequence, e.g., a linker sequence provided herein.

In some instances, a polypeptide for use in the methods disclosed herein may be a polypeptide comprising a contiguous amino acid sequence having at least 85% sequence identity (e.g., at least 90%, at least 93%, at least 95%, at least 98%, at least 99%, or 100% sequence identity) to residues 80-198 of SEQ ID NO:1 and, e.g., may be represented by the amino acid sequence LGQEVSRGRDAAQEL-RASLLETQMEEDILQLQAEATAEVLGEVAQAQKVL-RDSVQRLE VQLRSAWLGPAYREFEVLKAHAD-KQSHILWALTGHVQRQRREMVAQQHRLRQIQERL HTAALPA (SEQ ID NO: 5).

In some instances, a polypeptide for use in the methods disclosed herein may be a polypeptide comprising an amino acid sequence having at least 85% sequence identity (e.g., at least 90%, at least 93%, at least 95%, at least 98%, at least 99%, or 100% sequence identity) to:
MPVPALCLLWALAMVTRPASAVSRGRDAAQEL-RASLLETQMEEDILQL QAEATAEVLGEVAQAQKVL-RDSVQRLEVQLRSAWLGPAYREFEVLKAHAD-KQSHILW ALTGHVQRQRREMVAQQHRLR QIQERLHTAALPA (SEQ ID NO: 16)

In certain embodiments of the present disclosure, an ANGPTL8 of the instant disclosure may be a ANGPTL8 derived from mouse ANGPTL8. The consensus protein sequence of mouse ANGPTL8 (Gm6484, NCBI RefSeq NP_001074409.1) is:

(SEQ ID NO: 6; the signal peptide is underlined)
MAVLALCLLWTLASAVRPAPVAPLGGPEPAQYEELTLLFHGALQLGQAL

NGVYRATEARLTEAGHSLGLYDRALEFLGTEVRQGQDATQELRTSLSEI

QVEEDALHLRAEATARSLGEVARAQQALRDTVRRLQVQLRGAWLGQAHQ

EFETLKARADKQSHLLWALTGHVQRQQREMAEQQQWLRQIQQRLHTAAL

PA.

Mouse ANGPTL8 contains a signal peptide from residues 1-15 of SEQ ID NO: 6 and a ANGPTL8 chain from resides 16-198 of SEQ ID NO: 6. In some instances, a ANGPTL8 peptide of interest may contain all or a portion of the C-terminal coiled-coil domain of mouse ANGPTL8 residues 77-198 of SEQ ID NO: 6 and, e.g., may be represented by the amino acid sequence (SEQ ID NO: 7)
LGTEVRQGQDATQELRTSLSEIQVEEDALHLRAEATARSLGEVARAQQA

LRDTVRRLQVQLRGAWLGQAHQEFETLKARADKQSHLLWALTGHVQRQQ

REMAEQQQWLRQIQQRLHTAALPA.

In some instances, a ANGPTL8 of the instant disclosure may be represented by one or more natural variants, e.g., as compared to the above described reference protein sequence or the reference DNA sequences provided above. Such natural variants will vary and may include, but are not limited to, a W for R substitution at position 59 of SEQ ID NO:1 and a Q for R substitution at position 147 of SEQ ID NO:1.

Variants of a ANGPTL8 of the instant disclosure may in some cases be represented by protein sequences having one or more amino acid deletions of varying length, including deletions ranging from 1-180 amino acids in length as compared to the ANGPTL8 protein sequence set forth in SEQ ID NO:1, including but not limited to deletions of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, or 180 amino acids in length. In some instances, a ANGPTL8 variant may contain an amino acid deletion of 59 amino acids in length from residues 21-79 of the ANGPTL8 protein sequence of SEQ ID NO:1.

Amino acid deletions of subject ANGPTL8 variants are not limited to internal amino acids or internal sequences of amino acids and in some instances may be represented by N-terminal or C-terminal truncations. For example, a ANGPTL8 variant of the instant disclosure may have a N-terminal truncation or a C-terminal truncation ranging anywhere from 1-180 amino acids in length, including but not limited to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, or 180 amino acids in length. In certain instances, a ANGPTL8 variant of the subject disclosure may represent an N-terminal deletion of amino acids 1-79 of the ANGPTL8 of SEQ ID NO:1.

In certain embodiments of the present disclosure, a peptide of interest in the instant disclosure may be derived from a ANGPTL8 related gene or contain a portion of a ANGPTL8 related protein. In certain instances, a peptide of the instant disclosure may be derived from one or more angiopoietin (ANG) family proteins, e.g., including but not limited to angiopoietin-1 (ANG-1, GenBank: AAM92271.1), angiopoietin-2 (ANG-2, GenBank: AAI43903.1), angiopoietin-3 (ANG-3, GenBank: AAD31728.1), angiopoietin-4 (ANG-4, GenBank: AAI11977.1), angiopoietin-like Protein 1 (ANGPTL1; GenBank: AAH50640.1), angiopoietin-like Protein 2 (ANGPTL2; GenBank: AIC50961.1), angiopoietin-like Protein 3 (ANGPTL3; GenBank: AAH07059.1), angiopoietin-like Protein 4 (ANGPTL4; GenBank: AIC56388.1), angiopoietin-like Protein 5 (ANGPTL5; GenBank: AAQ89186.1), angiopoietin-like Protein 6 (ANGPTL6; GenBank: AAI42633.1) and angiopoietin-like Protein 7 (ANGPTL7; GenBank: AIC50550.1). For example, in certain embodiments a subject polypeptide of the instant disclosure may be derived from or contain a portion of a human angiopoietin-like 2 polypeptide (AAH12368.1) of the amino acid sequence:

(SEQ ID NO: 8)
MRPLCVTCWWLGLLAAMGAVAGQEDGFEGTEEGSPREFIYLNRYKRAGE

SQDKCTYTFIVPQQRVTGAICVNSKEPEVLLENRVHKQELELLNNELLK

QKRQIETLQQLVEVDGGIVSEVKLLRKESRNMNSRVTQLYMQLLHEIIR

KRDNALELSQLENRILNQTADMLQLASKYKDLEHKYQHLATLAHNQSEI

IAQLEEHCQRVPSARPVPQPPPAAPPRVYQPPTYNRIINQISTNEIQSD

QNLKVLPPPLPTMPTLTSLPSSTDKPSGPWRDCLQALEDGHDTSSIYLV

KPENTNRLMQVWCDQRHDPGGWTVIQRRLDGSVNFFRNWETYKQGFGNI

DGEYWLGLENIYWLTNQGNYKLLVTMEDWSGRKVFAEYASFRLEPESEY

YKLRLGRYHGNAGDSFTWHNGKQFTTLDRDHDVYTGNCAHYQKGGWWYN

ACAHSNLNGVWYRGGHYRSRYQDGVYWAEFRGGSYSLKKVVMMIRPNPN

TFH.

In some instances, peptides of the instant disclosure that contain a peptide of a ANGPTL8 related protein may contain only a portion or a particular domain or a portion of a particular domain of the ANGPTL8 related protein. For example, in one embodiment, a peptide of interest may contain a portion of a human angiopoietin-like 2 polypeptide, e.g., represented by the amino acid sequence (SEQ ID NO: 9)
LENRVHKQELELLNNELLKQKRQIETLQQLVEVDGGIVSEVKLLRKESR

NMNSRVTQLYMQLLHEIIRKRDNALELSQLENRILNQTADMLQLASKYK

DLEHKYQHLATLAHNQSEIIA.

Nucleic Acid and Protein Sequences

The subject polypeptide may be generated using recombinant techniques to manipulate nucleic acids of different ANGPTL8 known in the art to provide constructs encoding a protein of interest. It will be appreciated that, provided an amino acid sequence, the ordinarily skilled artisan will immediately recognize a variety of different nucleic acids encoding such amino acid sequence in view of the knowledge of the genetic code.

In some instances, a ANGPTL8 of the instant disclosure may be expressed from a fragment of the recombinant cDNA having the sequence:

(SEQ ID NO: 4)
ATGCCAGTGCCTGCTCTGTGCCTGCTCTGGGCCCTGGCAATGGTGACCC

GGCCTGCCTCAGCGGCCCCCATGGGCGGCCCAGAACTGGCACAGCATGA

GGAGCTGACCCTGCTCTTCCATGGGACCCTGCAGCTGGGCCAGGCCCTC

AACGGTGTGTACAGGACCACGGAGGGACGGCTGACAAAGGCCAGGAACA

GCCTGGGTCTCTATGGCCGCACAATAGAACTCCTGGGGCAGGAGGTCAG

CCGGGGCCGGGATGCAGCCCAGGAACTTCGGGCAAGCCTGTTGGAGACT

CAGATGGAGGAGGATATTCTGCAGCTGCAGGCAGAGGCCACAGCTGAGG

TGCTGGGGGAGGTGGCCCAGGCACAGAAGGTGCTACGGGACAGCGTGCA

GCGGCTAGAAGTCCAGCTGAGGAGCGCCTGGCTGGGCCCTGCCTACCGA

GAATTTGAGGTCTTAAAGGCTCACGCTGACAAGCAGAGCCACATCCTAT

GGGCCCTCACAGGCCACGTGCAGCGGCAGAGGCGGGAGATGGTGGCACA

GCAGCATCGGCTGCGACAGATCCAGGAGAGACTCCACACAGCGGCGCTC

CCAGCCTGA or variants thereof, including but not limited to variants having one or more silent mutations of the above cDNA sequence, including, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, and 190-200 silent mutations.

The skilled artisan will readily recognize that the protein and gene features disclosed herein with reference to human ANGPTL8 may be independently located on or the presence or absence of such features in a related gene or protein determined by amino acid or nucleotide alignment of related the related sequence to the appropriate human reference sequence. Exemplary related homologous gene sequences to human ANGPTL8 include but are not limited to C19H19orf80 of *P. troglodytes*, C20H19orf80 of *C. lupus*, C7H19orf80 of *B. taurus*, Gm6484 of *M. musculus*, and LOC100361444 of *R. norvegicus*. Exemplary related homologous protein sequences to human ANGPTL8 include but are not limited to XP_003316163.1, XP_005632923.1, XP_005208869.1, NP_001074409.1 and NP_001258639.1.

Further paralogous genes related to human ANGPTL8 include but are not limited to c1g8h19orf80 of *Poecilia reticulata*, c2h19orf80 of *Anolis carolinensis*, C6H19orf80 of *Chlorocebus sabaeus*, C3H19orf80 of *Monodelphis domestica*, CA2H19orf80 of *Felis catus*, C7H19orf80 of *Capra hircus*, C7H19orf80 of *Equus caballus*, C19H19orf80 of *Macaca fascicularis*, C5H19orf80 of *Microtus ochrogaster*, C19H19orf80 of *Gorilla gorilla*, C19H19orf80 of *Papio anubis*, LOC102508050 of *Camelus ferus*, C22H19orf80 of *Callithrix jacchus*, LOC103783638 of *Pan paniscus*, LOC103734570 of *Nannospalax galili*, LOC103678678 of *Ursus maritimus*, LOC103591351 of *Galeopterus variegatus*, LOC103543218 of *Equus przewalskii*, LOC103301110 of *Eptesicus fuscus*, LOC103249447 of *Tarsius syrichta*, LOC103207899 of *Orycteropus afer afer*, LOC103170718 of *Ornithorhynchus anatinus*, LOC103162524 of *Cricetulus griseus*, LOC103007216 of *Balaenoptera acutorostrata scammoni*, LOC102983429 of *Physeter catodon*, LOC102964797 of *Panthera tigris altaica*, LOC102906929 of *Peromyscus maniculatus bairdii*, LOC102888052 of *Pteropus alecto*, LOC102862909 of *Elephantulus edwardii*, LOC102759590 of *Myotis davidii*, LOC102747799 of *Leptonychotes weddellii*, LOC102483995 of *Tupaia chinensis*, LOC102440177 of *Myotis lucifugus*, LOC102416148 of *Bubalus bubalis*, LOC102335494 of *Pantholops hodgsonii*, LOC102267376 of *Bos mutus*, LOC102244580 of *Myotis brandtii*, LOC102016286 of *Chinchilla lanigera*, LOC101972143 of *Ictidomys tridecemlineatus*, LOC101826982 of *Mesocricetus auratus*, LOC101706461 of *Heterocephalus glaber*, LOC101670309 of *Mustela putorius furo*, LOC101660529 of *Echinops telfairi*, LOC101599511 of *Jaculus jaculus*, LOC101568418 of *Octodon degus*, LOC101392854 of *Ceratotherium simum simum*, LOC101362133 of *Odobenus rosmarus divergens*, LOC101350564 of *Trichechus manatus latirostris*, LOC101336653 of *Tursiops truncatus* and LOC101284684 of *Orcinus orca*.

Protein Modifications

The proteins used in the present disclosure can be provided as proteins that are modified. Purposes of the modifications may be to increase a property desirable in a protein formulated for therapy (e.g. serum half-life), to raise antibody for use in detection assays, and/or for protein purification, and the like.

One way to modify a subject protein is to conjugate (e.g. link) one or more additional elements at the N- and/or C-terminus of the protein, such as another protein (e.g. having an amino acid sequence heterologous to the subject protein) and/or a carrier molecule. Thus, an exemplary protein can be provided as a fusion protein with a polypeptide(s) derived from an immunoglobulin Fc polypeptide.

Conjugate modifications to proteins may result in a protein that retains the desired activity, while exploiting properties of the second molecule of the conjugate to impart and/or enhance certain properties (e.g. desirable for therapeutic uses). For example, the polypeptide may be conjugated to a molecule, e.g., to facilitate solubility, storage, half-life, reduction in immunogenicity, controlled release in tissue or other bodily location (e.g., blood or other particular organs, etc.).

Other features of a conjugated protein may include one where the conjugate reduces toxicity relative to an unconjugated protein. Another feature is that the conjugate may target a type of cell or organ more efficiently than an unconjugated material. The protein can optionally have attached a drug to further counter the causes or effects associated with disorders of metabolism (e.g., drug for decreasing triglyceride level), and/or can optionally be modified to provide for improved pharmacokinetic profile (e.g., by PEGylation, hyperglycosylation, and the like).

In certain embodiments, the polypeptide sequences disclosed herein may be conjugated to a heterologous polypeptide that increases in vivo hale life (e.g., serum half) and/or solubility (e.g., decrease aggregate formation when expressed from a host cell line or decrease aggregation during purification from a host cell line).

Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules can be about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1, 2, 3, 4, 5, 6, 7, 8, 9, 10, 10-20, 20-30, 30-50 amino acids.

Exemplary flexible linkers include glycine polymers $(G)_n$, glycine-alanine polymers, alanine-serine polymers, glycine-serine polymers (for example, $(G_mS_o)_n$, $(GSGGS)_n$ (SEQ ID NO: 18), $(G_mS_oG_m)_n$, $(G_mS_oG_mS_oG_m)_n$ (SEQ ID NO: 19), $(GSGGS_m)_n$ (SEQ ID NO: 20), $(GSGS_mG)_n$ (SEQ ID NO: 21) and $(GGGS_m)_n$ (SEQ ID NO: 22), and combinations thereof, where m, n, and o are each independently selected from an integer of at least 1 to 20, e.g., 1-18, 2-16, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components. Exemplary flexible linkers include, but are not limited to GGSG (SEQ ID NO: 23), GGSGG (SEQ ID NO: 24), GSGSG (SEQ ID NO: 25), GSGGG (SEQ ID NO: 26), GGGSG (SEQ ID NO: 27), and GSSSG (SEQ ID NO: 28).

Additional flexible linkers include glycine polymers $(G)_n$ or glycine-serine polymers (e.g., $(GS)_n$, $(GSGGS)_n$ (SEQ ID NO: 18), $(GGGS)_n$ (SEQ ID NO: 29) and $(GGGGS)_n$ (SEQ ID NO: 32), where n=1 to 50, for example, 1, 2, 3, 4, 5, 6, 7, 8, 9, 10, 10-20, 20-30, 30-50. Exemplary flexible linkers include, but are not limited to GGGS (SEQ ID NO: 31), GGGGS (SEQ ID NO: 32), GGSG (SEQ ID NO: 23), GGSGG (SEQ ID NO: 24), GSGSG (SEQ ID NO: 25), GSGGG (SEQ ID NO: 26), GGGSG (SEQ ID NO: 27), and GSSSG (SEQ ID NO: 28). A multimer (e.g., 1, 2, 3, 4, 5, 6, 7, 8, 9, 10, 10-20, 20-30, or 30-50) of these linker sequences may be linked together to provide flexible linkers that may be used to conjugate a heterologous amino acid sequence to the polypeptides disclosed herein. As described herein, the heterologous amino acid sequence may be a signal sequence and/or a fusion partner, such as, albumin, Fc sequence, and the like.

Methods of Production

The proteins of the present disclosure can be produced by any suitable method, including recombinant and non-recombinant methods (e.g., chemical synthesis). Where a polypeptide is chemically synthesized, the synthesis may proceed via liquid-phase or solid-phase. Solid-phase synthesis (SPPS) allows the incorporation of unnatural amino acids and/or peptide/protein backbone modification. Various forms of SPPS, such as Fmoc and Boc, are available for synthesizing peptides of the present disclosure. Details of the chemical synthesis are known in the art (e.g. Ganesan A. 2006 *Mini Rev. Med Chem.* 6:3-10 and Camarero J A et al. 2005 *Protein Pept Lett.* 12:723-8). Briefly, small insoluble, porous beads are treated with functional units on which peptide chains are built. After repeated cycling of coupling/deprotection, the free N-terminal amine of a solid-phase attached peptide is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Where the protein is produced using recombinant techniques, the proteins may be produced as an intracellular protein or as a secreted protein, using any suitable construct and any suitable host cell, which can be a prokaryotic or eukaryotic cell, such as a bacterial (e.g. *E. coli*) or a yeast host cell, respectively.

Other examples of eukaryotic cells that may be used as host cells include insect cells, mammalian cells, and/or plant cells. Where mammalian host cells are used, the cells may include one or more of the following: human cells (e.g. HeLa, 293, H9 and Jurkat cells); mouse cells (e.g., NIH3T3, L cells, and C127 cells); primate cells (e.g. Cos 1, Cos 7 and CV1) and hamster cells (e.g., Chinese hamster ovary (CHO) cells).

In certain embodiments, the subject proteins when expressed in a cell may include a signal sequence which may be cleaved off when the protein is secreted out of the cell.

A wide range of host-vector systems suitable for the expression of the subject protein may be employed according to standard procedures known in the art. See for example, Sambrook et al. 1989 *Current Protocols in Molecular Biology* Cold Spring Harbor Press, New York and Ausubel et al. 1995 *Current Protocols in Molecular Biology*, Eds. Wiley and Sons.

Methods for introduction of genetic material into host cells include, for example, transformation, electroporation, conjugation, calcium phosphate methods and the like. The method for transfer can be selected so as to provide for stable expression of the introduced ANGPTL8-encoding nucleic acid. The polypeptide-encoding nucleic acid can be provided as an inheritable episomal element (e.g., plasmid) or can be genomically integrated. A variety of appropriate vectors for use in production of a polypeptide of interest are available commercially.

Vectors can provide for extrachromosomal maintenance in a host cell or can provide for integration into the host cell genome. The expression vector provides transcriptional and translational regulatory sequences, and may provide for inducible or constitutive expression, where the coding region is operably linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, CMV, and the like). In certain embodiments, the proteins of the present disclosure may be expressed from a nucleic acid construct in which a heterologous promoter is operably linked to a nucleic acid sequence encoding the protein.

Expression constructs generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture, by immunoaffinity purification, which generally involves contacting the sample with an anti-protein antibody, washing to remove non-specifically bound material, and eluting the specifically bound protein. The isolated protein can be further purified by dialysis and other methods normally employed in protein purification methods. In one embodiment, the protein may be isolated using metal chelate chromatography methods. Protein of the present disclosure may contain modifications to facilitate isolation, as discussed above.

The subject proteins may be prepared in substantially pure or isolated form (e.g., free from other polypeptides). The protein can be present in a composition that is enriched for the polypeptide relative to other components that may be present (e.g., other polypeptides or other host cell components). Purified protein may be provided such that the protein is present in a composition that is substantially free of other expressed proteins, e.g., less than 90%, usually less than 60% and more usually less than 50% of the composition is made up of other expressed proteins.

Compositions

The present disclosure provides compositions comprising a subject protein, which may be administered to a subject in need of reducing one or more of triglyceride levels, total cholesterol levels, and LDL levels. In certain cases, the composition may include a subject polypeptide as described herein and a pharmaceutically acceptable excipient.

The polypeptides of the present disclosure may be in the form of compositions suitable for administration to a subject. In general, such compositions are "pharmaceutical compositions" comprising one or more polypeptides and one or more pharmaceutically acceptable or physiologically acceptable diluents, carriers or excipients. In certain embodiments, the polypeptides are present in a therapeutically effective amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions may be used in combination with other therapeutically active agents or compounds (e.g., an appetite suppressing agent) in order to treat or prevent the diseases, disorders and conditions as contemplated by the present disclosure.

The pharmaceutical compositions typically comprise a therapeutically effective amount of at least one of the polypeptides contemplated by the present disclosure and one or more pharmaceutically or physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that could be used in the pharmaceutical compositions and dosage forms. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver the polypeptides, including implants (e.g., implantable pumps) and catheter systems, both of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

The pharmaceutical compositions containing the active ingredient (e.g., polypeptides of the present disclosure) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods of preparing liposomes are described in, for example, U.S. Pat. Nos. 4,235,871, 4,501,728, and 4,837,028. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally-occurring gums, for example, gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The present disclosure contemplates the administration of the polypeptides in the form of suppositories for rectal administration of the drug. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The polypeptides contemplated by the present disclosure may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Contemplated herein is the use of Nano Precision Medical's depot delivery technology (Nano Precision Medical; Emeryville, Calif.). The technology utilizes a titania nanotube membrane that produces zero-order release rates of macromolecules, such as protein and peptide therapeutics. The biocompatible membrane is housed in a small, subcutaneous implant that provides long-term (e.g., up to one year), constant-rate delivery of therapeutic macromolecules. The technology is currently being evaluated for the delivery of GLP-1 agonists for the treatment of Type II diabetes. In certain embodiments, the polypeptide(s) disclosed herein may be a formulation with a membrane. For example, the polypeptide may be impregnated into the membrane or surrounded by the membrane. The membrane may be in shape of a disc, tube or sphere. In certain embodiments, the tube may be a nanotube or the sphere may be a nanosphere.

A subject pharmaceutical composition can include a polypeptide as provided herein. For example, the subject pharmaceutical composition can include a polypeptide comprising a contiguous amino acid sequence having at least 85% sequence identity (e.g., at least 90%, at least 93%, at least 95%, at least 98%, at least 99%, or 100% sequence identity) to the amino acid sequence of amino acids 80-198 of full-length ANGPTL8 (SEQ ID NO. 1), wherein the polypeptide lacks the amino acids 21-75 of full-length ANGPTL8 (SEQ ID NO: 1); and a pharmaceutically acceptable excipient.

Patient Populations

The present disclosure provides a method for reducing triglyceride levels in a subject having elevated triglyceride levels. The present disclosure provides a method for reducing total cholesterol levels in a subject having elevated total cholesterol levels. Exemplary methods include reducing LDL cholesterol levels in a subject having high LDL cholesterol levels.

Elevated triglyceride levels are associated with conditions such as cardiovascular disease, heart disease, myocardial infarction, stroke, atherosclerosis, diabetes, chronic renal disease, hyperlipidemias, pancreatitis, chylomicronemia, eruptive xanthomata and abdominal pain. Severe hypertriglyceridemia, in particular, is associated with chylomicronemia and eruptive xanthomata, abdominal pain, and/or pancreatitis. High triglyceride levels, in particular, are associated with diabetes mellitus, chronic renal disease, certain primary hyperlipidemias. In addition, elevated triglyceride levels are a compounding factor for conditions that increase the risk of cardiovascular disease including obesity, hypertension, and cigarette smoking.

Hyperlipoproteinemia associated with elevated triglyceride levels may be secondary hyperlipoproteinemia. Secondary hyperlipoproteinemia associated with elevated triglyceride levels is associated with and a compounding factor of several conditions, such as obesity, excessive alcohol intake, and the use of a variety of drugs, including thiazide diuretics, oral contraceptives and other estrogens, and some beta-adrenergic blocking drugs. In addition, secondary hyperlipoproteinemia associated with elevated triglyceride levels is further associated with diabetes mellitus, hypothyroidism, renal disease (uremia, nephrotic syndrome, maintenance dialysis, and renal transplantation), liver disease, dysproteinemias, and other metabolic and endocrine diseases.

Elevated triglyceride levels are also associated with acute stress associated conditions. Acute stress associated states associated with elevated triglyceride levels include but are not limited to burns, trauma, myocardial infarction and sepsis.

Elevated triglyceride levels may, in some instances, be the result of one or more familial or genetic conditions either directly or indirectly. In some instances, such familial or genetic conditions do not respond to direct or indirect treatment of elevated triglyceride levels. Persistent hypertriglyceridemia, including hypertriglyceridemia that persists despite treatment of the underlying condition, may be associated with or caused by a primary form of hyperlipoproteinemia, such as familial hypertriglyceridemia. Further familiar conditions associated with elevated triglyceride levels include familial combined lipidemia and familial dysbetalipoproteinemia (Type III hyperlipoproteinemia).

High cholesterol levels (total cholesterol and LDL cholesterol) are strongly associated with cardiovascular disease because these promote atheromatous plaques development in arteries (atherosclerosis). This disease process may lead to myocardial infarction (heart attack), stroke, and peripheral vascular disease.

As such, patients with any of the above listed conditions may be treated by administering the polypeptides described herein.

It is understood that the conditions listed herein are exemplary and not meant to limit the conditions that may be treated using the compositions described herein. As such, patients having other conditions may also be treated using the compositions provided herein.

Methods

The subject methods involve administering the subject proteins to a patient who has elevated triglyceride levels. As used herein "elevated triglyceride levels" or "high triglyceride levels" refer to triglyceride levels greater than an optimal level of triglycerides in a body fluid sample of a human. The American Heart Association (AHA) recommends that a triglyceride level of 100 mg/dL or lower is considered optimal. "Elevated triglyceride levels" or "high triglyceride levels" refer to triglyceride levels greater than 100 mg/dL, e.g., greater than 150 mg/dL, 200 mg/dL, 250 mg/dL, 300 mg/dL, 350 mg/dL, 400 mg/dL, 450 mg/dL, or 500 mg/dL, or more.

The subject methods involve administering the proteins disclosed herein to a patient who has triglyceride levels greater than 100 mg/dL, e.g., greater than about 150 mg/dL, 200 mg/dL, 250 mg/dL, 300 mg/dL, 350 mg/dL, 400 mg/dL, 450 mg/dL, 500 mg/dL or more in a body fluid sample of the patient.

Subjects having, suspected of having, or at risk of developing elevated triglyceride levels can be administered a polypeptide as described herein to treat the patient. Subjects who have family history of elevated triglyceride levels or lifestyle, such as a sedentary lifestyle and/or a diet high in triglycerides, that may lead to elevated triglyceride levels can be considered as at risk of developing elevated triglyceride levels.

The present disclosure provides a method for reducing total cholesterol levels in a subject having elevated total cholesterol levels. As used herein, "elevated total cholesterol levels" or "high total cholesterol levels" refer to total cholesterol levels that are higher than normal total cholesterol levels of about less than 200 mg/dL. Elevated total cholesterol levels encompass levels higher than 200 mg/dL, e.g., 210 mg/dL, 220 mg/dL, 240 mg/dL, 250 mg/dL, or more.

The present disclosure provides a method for reducing LDL cholesterol levels in a subject having elevated LDL cholesterol levels. As used herein, "elevated LDL cholesterol levels" or "high LDL cholesterol levels" refer to LDL levels above 70 mg/dL, e.g., above 100 mg/dL, 120 mg/dL, 130 mg/dL, 150 mg/dL, 160 mg/dL, 180 mg/dL, 190 mg/dL, or more.

Patients with any of the above listed conditions may have elevated total cholesterol and/or LDL cholesterol. In certain cases, the present method may be used to reduce total cholesterol and/or LDL cholesterol in a patient who is at risk for heart disease or has heart disease. Subjects who have family history of elevated total cholesterol and/or LDL cholesterol or lifestyle, such as a sedentary lifestyle and/or a diet high in cholesterol, that may lead to elevated total cholesterol and/or LDL cholesterol levels can be considered as at risk of developing elevated total cholesterol and/or LDL cholesterol levels.

By "treatment" is meant that at least an amelioration of the symptoms associated with the condition afflicting the host is achieved, where amelioration refers to at least a reduction in the magnitude of a parameter, e.g. symptom, associated with the condition being treated. As such, treatment includes situations where the condition, or at least symptoms associated therewith, are reduced or avoided. Thus treatment includes: (i) prevention, that is, reducing the risk of development of clinical symptoms, including causing the clinical symptoms not to develop, e.g., preventing disease progression to a harmful or otherwise undesired state; (ii) inhibition, that is, arresting the development or further development of clinical symptoms, e.g., mitigating or completely inhibiting an active disease.

In the methods of the present disclosure, protein compositions described herein can be administered to a subject (e.g. a human patient) to, for example, achieve and/or maintain a target triglyceride level, e.g., to reduce triglyceride level in the bloodstream to a range found in a healthy individual. Subjects for treatment include those having a condition as described herein.

The subject methods may achieve a reduction of at least 5% or more in the triglyceride levels of a subject being administered a polypeptide comprising a contiguous amino acid sequence having at least 85% sequence identity to the amino acid sequence of amino acids 80-198 of full-length ANGPTL8 (SEQ ID NO. 1), wherein the polypeptide lacks the amino acids 21-74 of full-length ANGPTL8 (SEQ ID NO: 1). For example, the administering of the subject polypeptide may reduce the triglyceride levels of the subject by at least 5%, 10%, 15%, 20%, 25%, 30%, 35%, 40%, 45%, or more.

Triglyceride levels may be measured using any standard assay. For example, triglyceride levels may be measured in saliva, urine, blood, serum or plasma sample of a subject by using an enzymatic assay, e.g., using a lipase. Any of the commercially available kits may be used measure triglyceride levels in a body fluid sample of a patient. In certain embodiments, the body fluid sample may be blood, serum, or plasma.

The subject methods may achieve a reduction of at least 5% or more in the total cholesterol and/or LDL cholesterol levels of a subject being administered a polypeptide that includes a contiguous amino acid sequence having at least 85% sequence identity to the amino acid sequence of amino acids 80-198 of full-length ANGPTL8 (SEQ ID NO. 1), where the polypeptide lacks the amino acids 21-74 of full-length ANGPTL8 (SEQ ID NO: 1). For example, the administering of the subject polypeptide may reduce the total cholesterol and/or LDL cholesterol levels of the subject by at least 5%, 10%, 15%, 20%, 25%, 30%, 35%, 40%, 45%, or more.

Routes of Administration

The present disclosure contemplates the administration of the disclosed polypeptides, and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. In certain embodiments, administration may be subcutaneous.

Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The present disclosure contemplates methods wherein the polypeptides of the present disclosure are administered to a subject at least twice daily, at least once daily, at least once every 48 hours, at least once every 72 hours, at least once weekly, at least once every 2 weeks, at least once monthly, at least once every 2 months, or at least once every 3 months, or less frequently.

Combination Therapy

Any of a wide variety of therapies directed to treating or preventing elevated triglyceride levels can be combined in a composition or therapeutic method with the subject proteins.

"Combination" as used herein is meant to include therapies that can be administered separately, e.g. formulated separately for separate administration (e.g., as may be provided in a kit), as well as for administration in a single formulation (i.e., "co-formulated"). Examples of agents that may be provided in a combination therapy include statins, fibrates, niacin, and fish oil.

Where the subject protein is administered in combination with one or more other therapies, the combination therapy can be administered anywhere from simultaneously to up to 5 hours or more, e.g., 10 hours, 15 hours, 20 hours or more, prior to or after administration of a subject protein. In certain embodiments, a subject protein and other therapeutic intervention are administered or applied sequentially, e.g., where a subject protein is administered before or after another therapeutic treatment. In yet other embodiments, a subject protein and other therapy are administered simultaneously, e.g., where a subject protein and a second therapy are administered at the same time, e.g., when the second therapy is a drug it can be administered along with a subject protein as two separate formulations or combined into a single composition that is administered to the subject. Regardless of whether administered sequentially or simultaneously, as illustrated above, the treatments are considered to be administered together or in combination for purposes of the present disclosure.

Dosages

In the methods described herein, a therapeutically effective amount of a subject protein is administered to a patient in need thereof. For example, a therapeutically effective amount of the subject protein causes the triglyceride levels to decrease by at least about 5% compared to the triglyceride levels determined prior to the treatment of the patient with the subject polypeptide. In certain cases, the subject protein causes return of triglyceride levels to a normal level when the subject protein is delivered to the bloodstream in an effective amount to a patient who did not have normal triglyceride levels prior to being treated.

In exemplary methods, a therapeutically effective amount of a subject protein is administered to a patient in need thereof. For example, a therapeutically effective amount of the subject protein causes the total cholesterol levels and/or LDL cholesterol levels to decrease by at least about 5% compared to the levels determined prior to the treatment of the patient with the subject polypeptide. In certain cases, the subject protein causes return of total cholesterol levels and/or LDL cholesterol levels to normal levels when the subject protein is delivered to the bloodstream in an effective amount to a patient who did not have normal total cholesterol levels and/or LDL cholesterol levels prior to being treated.

The amount administered varies depending upon the goal of the administration, the health and physical condition of the individual to be treated, age, the degree of resolution desired, the formulation of a subject protein, the activity of the subject proteins employed, the treating clinician's assessment of the medical situation, the condition of the subject, and the body weight of the subject, as well as the severity of the condition, and other relevant factors. The size of the dose will also be determined by the existence, nature, and extent of any adverse side-effects that might accompany the administration of a particular protein.

It is expected that the amount will fall in a relatively broad range that can be determined through routine trials. For example, the amount of subject protein employed to decrease one or more of triglycerides, total cholesterol and LDL cholesterol is not more than about the amount that could otherwise be irreversibly toxic to the subject (i.e., maximum tolerated dose). In other cases, the amount is around or even well below the toxic threshold, but still in an effective concentration range, or even as low as threshold dose.

Individual doses are typically not less than an amount required to produce a measurable effect on the subject, and may be determined based on the pharmacokinetics and pharmacology for absorption, distribution, metabolism, and excretion ("ADME") of the subject protein or its by-products, and thus based on the disposition of the composition within the subject. This includes consideration of the route of administration as well as dosage amount, which can be adjusted for enteral (applied via digestive tract for systemic or local effects when retained in part of the digestive tract) or parenteral (applied by routes other than the digestive tract for systemic or local effects) applications. For instance, administration of a subject protein is typically via injection and often subcutaneous, intravenous, intramuscular, or a combination thereof.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors.

In some embodiments, the effective amount is the same as the calculated $ED_{50}$, and in certain embodiments the effective amount is an amount that is more than the calculated $ED_{50}$. In certain embodiments the effective amount is an amount that is less than the calculated $ED_{50}$.

An effective amount of a protein may also be an amount that is effective, when administered in one or more doses, to decrease triglyceride levels of an individual by at least about 5%, at least about 10%, at least about 20%, at least about 25%, at least about 30%, at least about 40%, at least about 50%, at least about 60%, at least about 70%, at least about 80%, or more than 80%, compared to triglyceride levels in the individual prior to the treatment.

Further examples of dose per administration may be at less than 10 µg, less than 2 µg, or less than 1 µg. Dose per administration may also be more than 50 µg, more than 100 µg, more than 300 µg up to 600 µg or more. An example of a range of dosage per weight is about 0.1 µg/kg to about 1 µg/kg, up to about 1 mg/kg or more. Effective amounts and dosage regimens can readily be determined empirically from assays, from safety and escalation and dose range trials, as well as in vitro and in vivo assays known in the art.

The term "unit dosage form," as used herein, refers to physically discrete units suitable as unitary dosages for human and animal subjects, each unit containing a predetermined quantity of proteins of the present disclosure calculated in an amount sufficient to produce the desired effect in association with a pharmaceutically acceptable diluent, carrier or vehicle. The specifications for the novel unit dosage forms depend on the particular protein employed and the effect to be achieved, and the pharmacodynamics associated with each protein in the host.

Kits

Also provided by the present disclosure are kits for using the compositions disclosed herein and for practicing the methods, as described above. The kits may be provided for administration of the subject protein in a subject in need of treatment or prevention of one or more of high triglyceride levels, high total cholesterol levels, and high LDL cholesterol. The kit can include one or more of the proteins disclosed herein, which may be provided in a sterile container, and can be provided in a formulation with a suitable pharmaceutically acceptable excipient for administration to a subject. The proteins can be provided with a formulation that is ready to be used as it is or can be reconstituted to have the desired concentrations. Where the proteins are provided to be reconstituted by a user, the kit may also provide buffers, pharmaceutically acceptable excipients, and the like, packaged separately from the subject protein. The proteins of the present kit may be formulated separately or in combination with other drugs.

In addition to above-mentioned components, the kits can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Materials and Methods

Construction of AAV Vectors:

Polymerase chain reaction (PCR) was conducted according to manufacturer's instructions. PCR reagents kits with Phusion® high-fidelity DNA polymerase were purchased from New England BioLabs (F-530L, Ipswich, Mass.). The reactions were set up according to manufacturer's instructions. Amplified DNA fragments containing full-length hANGPTL8 and variants thereof were digested with restriction enzymes XbaI and BamHI (or XbaI and BglII for ANGPTL8-V2) and were then ligated with AAV transgene vectors that had been digested with the same restriction enzymes. The vector used for expression contained a selectable marker and an expression cassette composed of a strong eukaryotic promoter 5' of a site for insertion of the cloned coding sequence, followed by a 3' untranslated region and bovine growth hormone polyadenylation tail. The expression construct is also flanked by internal terminal repeats at the 5' and 3' ends.

The PCR primer sequences were as follows:

```
ANGPTL8:
Forward:
                                      (SEQ ID NO: 10)
TACATATCTAGAATGCCAGTGCCTGCTCTGTG Reverse:
                                      (SEQ ID NO: 11)
CGCGGATCCTCAGGCTGGGAGCGCCGC ANGPTL8-V1:
Forward:
                                      (SEQ ID NO: 12)
TACATATCTAGAATGCCAGTGCCTGCTCTGTG Reverse:
                                      (SEQ ID NO: 13)
CGCGGATCCTCACTCCTGCCCCAGGAGTTC
```

Mouse Model:

Six-week old male C57BL/6 mice (Research Diets, catalog #D12492NI) received a one-time tail vein injection of recombinant AAV (rAAV). Mouse body weight and serum triglyceride levels were determined at various time points.

Plasma Triglyceride Assay:

Plasma was collected by tail snip. Triglyceride was measured using L-type triglyceride M kit following manufacturer's instruction.

Oral Lipid Tolerance Test:

Mice were gavaged with 10 μL/g corn oil (Mazola corn oil by ACH food companies, Inc., Memphis, Tenn.). Tail blood was collected at 0, 80, 145 minutes after corn oil. Triglyceride was measured using L-type triglyceride M kit following manufacturer's instruction.

VLDL Secretion Test:

Mice were injected with 10 μL/g of Tyloxapol (Sigma, St. Louis, Mo.) to block endogenous LPL activity. Tail blood was collected at 1 h, 2 h, and 4.5 h after injection. Triglyceride levels were measured using L-type triglyceride M kit (Wako Chemicals, Richmond, Va.) following manufacturer's instruction.

Example 1: Overexpression of ANGPTL8 by AAV in Mice

This example describes the metabolic effect of ANGPTL8 in mice treated with an adeno-associated virus (AAV) vector overexpressing either mouse or human full-length ANGPTL8. AAVs were injected through the tail vein into mice. Plasma triglyceride levels were measured in tail blood weekly. As shown in FIG. 1, overexpression of ANGPTL8 significantly increased plasma triglyceride (data shown are at week 4 post-injection, same trend was seen throughout the course of the study). Overexpression of another related family member, ANGPTL2, did not significantly affect plasma triglyceride levels.

Example 2: Overexpression of ANGPTL8-V2 Reduced Plasma Triglyceride in Mice

Figure 2A:
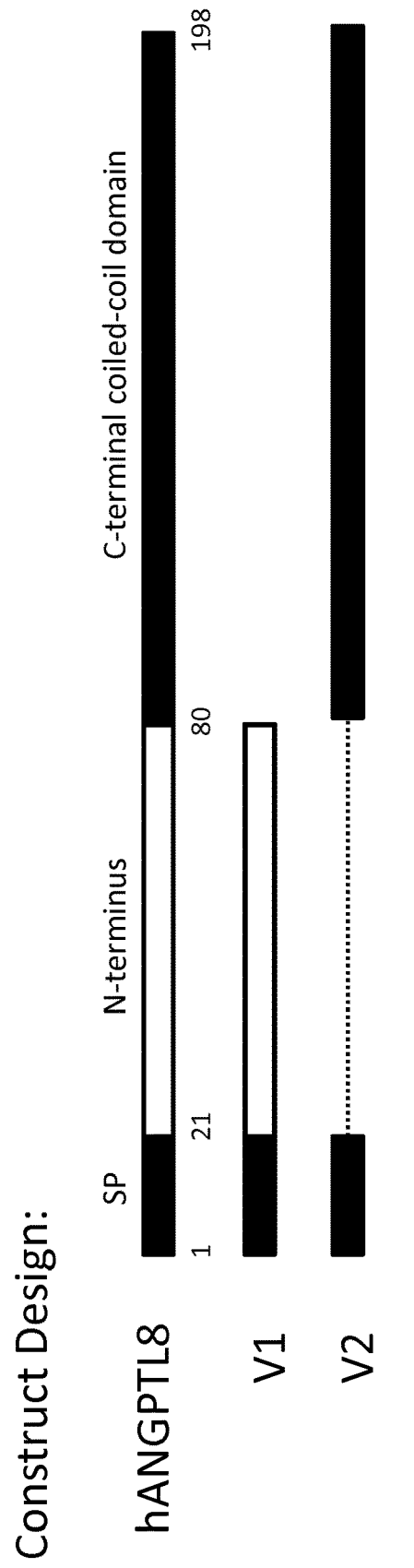
FIGS. 2A-2C indicate that an ANGPTL8 variant (ANGPTL8-V2) suppresses plasma triglyceride in mice.
Figure 2B:
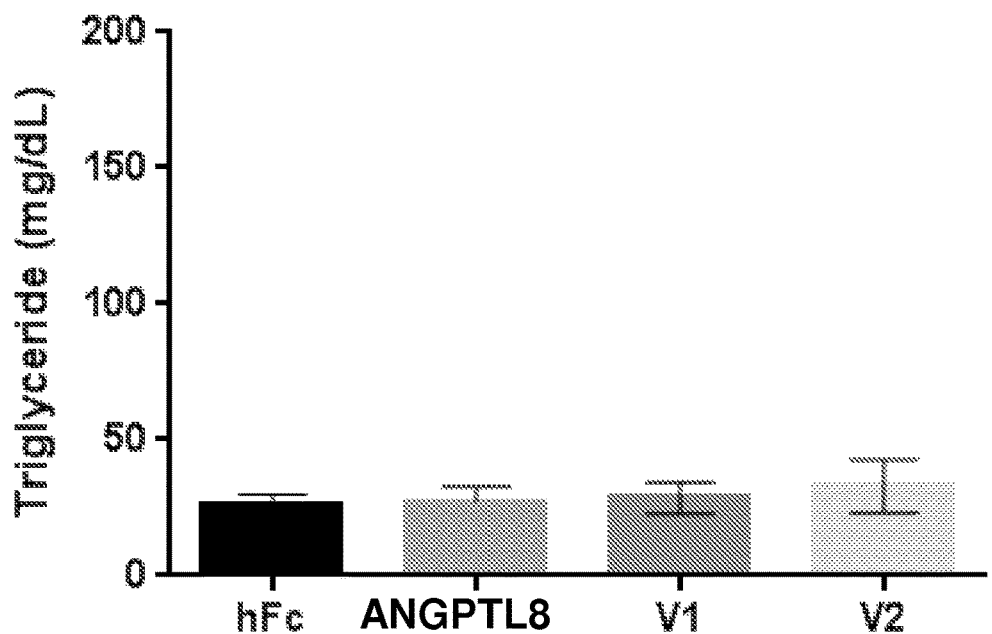
Figure 2C:
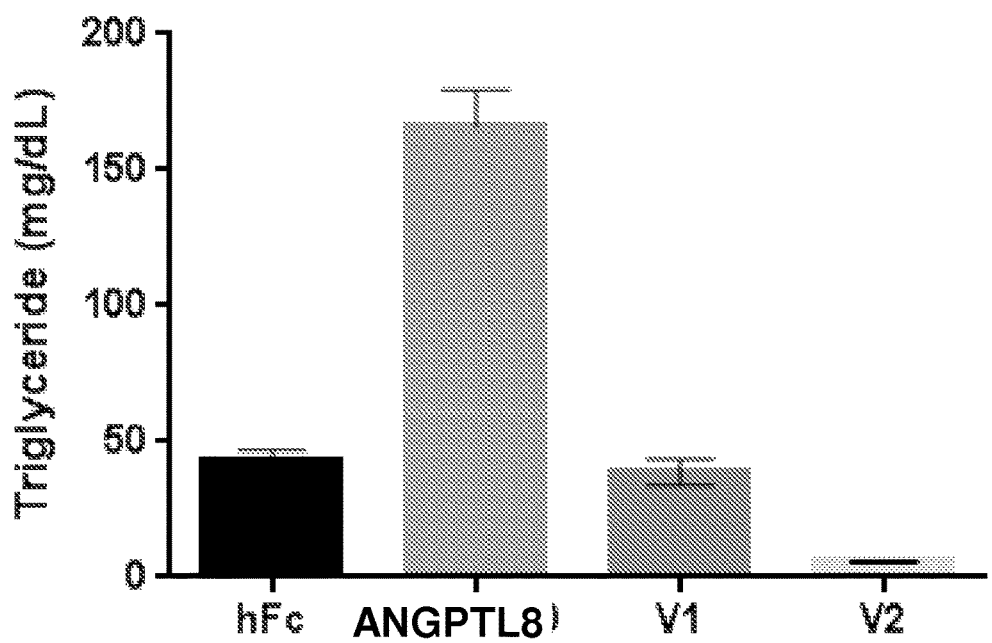

As depicted in FIG. 2A, variants of ANGPTL8 were made with deletion of either the N- or the C-terminus. Endogenous signal peptides (SP) were retained with both constructs. AAVs were injected through the tail vein into mice. Overexpression of full-length ANGPTL8 significantly increased plasma triglyceride levels (FIG. 2B-C). Conversely, overexpression of ANGPTL8-V1 did not affect levels of plasma triglycerides, suggesting that the C-terminus is essential for the triglyceride-raising action. Unexpectedly, overexpression of ANGPTL8-V2 resulted in marked suppression of plasma triglyceride. This shows that ANGPTL8-V2 functions as a dominant negative form.

Figure 3:
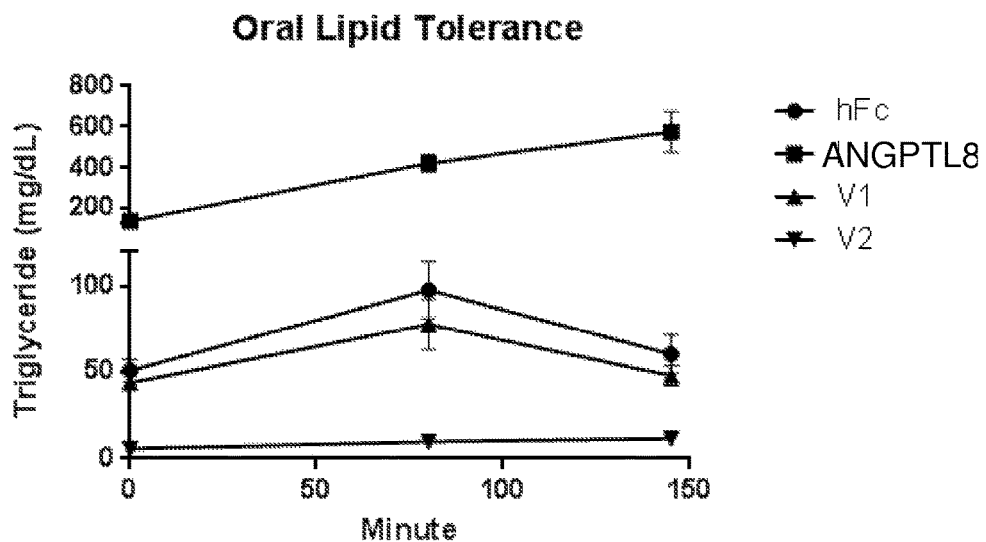
FIG. 3 indicates that overexpression of ANGPTL8 and ANGPTL8-V2 affected triglyceride absorption and/or clearance in mice.
Figure 4:
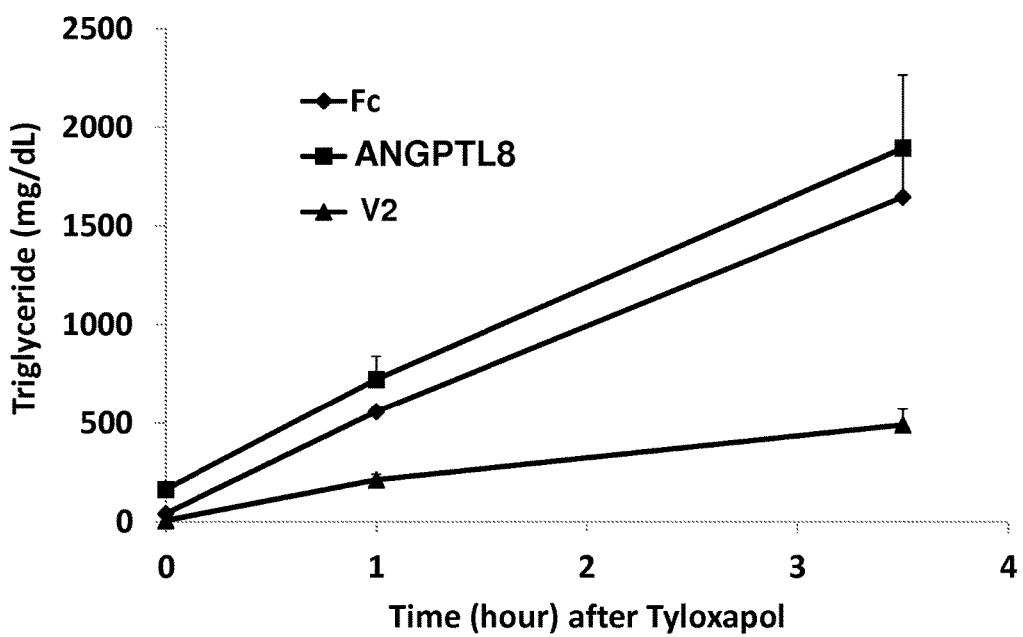
FIG. 4 indicates that overexpression of ANGPTL8-V2 reduced VLDL secretion in mice.

Example 3: Mechanism of Effect of ANGPTL8 and Variants on Plasma Triglyceride As depicted in FIG. 3, an oral lipid tolerance test was used to evaluate how variants of ANGPTL8 impact levels of plasma triglycerides. Overexpression of full-length ANGPTL8 greatly impaired the clearance of plasma triglyceride. In contrast, overexpression of ANGPTL8-V2 resulted in a dramatic improvement of lipid tolerance, suggesting the occurrence of reduced lipid absorption and/or enhanced clearance. Potential impact on very low density lipoportein (VLDL) secretion was also evaluated. Triglycerides are secreted by the liver as part of VLDL. In this test, endogeous triglyceride clearance was inhibited by applying a LPL inhibitor, Tyloxapol. Overexpression of ANGPTL8-V2 resulted in a markedly reduced accumulation of plasma triglycerides, suggesting that ANGPTL8-V2 suppresses VLDL secretion from the liver (FIG. 4).

The following sequences were used in these studies:

```
Full-length hANGPTL8:
                                            (SEQ ID NO: 1)
MPVPALCLLWALAMVTRPASAAPMGGPELAQHEELTLLFHGTLQLGQAL

NGVYRTTEGRLTKARNSLGLYGRTIELLGQEVSRGRDAAQELRASLLET

QMEEDILQLQAEATAEVLGEVAQAQKVLRDSVQRLEVQLRSAWLGPAYR

EFEVLKAHADKQSHILWALTGHVQRQRREMVAQQHRLRQIQERLHTAAL

PA

Full-length hANGPTL8 cDNA:
                                            (SEQ ID NO: 4)
ATGCCAGTGCCTGCTCTGTGCCTGCTCTGGGCCCTGGCAATGGTGACCC

GGCCTGCCTCAGCGGCCCCCATGGGCGGCCCAGAACTGGCACAGCATGA

GGAGCTGACCCTGCTCTTCCATGGGACCCTGCAGCTGGGCCAGGCCCTC

AACGGTGTGTACAGGACCACGGAGGGACGGCTGACAAAGGCCAGGAACA

GCCTGGGTCTCTATGGCCGCACAATAGAACTCCTGGGGCAGGAGGTCAG

CCGGGGCCGGGATGCAGCCCAGGAACTTCGGGCAAGCCTGTTGGAGACT

CAGATGGAGGAGGATATTCTGCAGCTGCAGGCAGAGGCCACAGCTGAGG

TGCTGGGGGAGGTGGCCCAGGCACAGAAGGTGCTACGGGACAGCGTGCA

GCGGCTAGAAGTCCAGCTGAGGAGCGCCTGGCTGGGCCCTGCCTACCGA

GAATTTGAGGTCTTAAAGGCTCACGCTGACAAGCAGAGCCACATCCTAT

GGGCCCTCACAGGCCACGTGCAGCGGCAGAGGCGGGAGATGGTGGCACA

GCAGCATCGGCTGCGACAGATCCAGGAGAGACTCCACACAGCGGCGCTC

CCAGCCTGA

ANGPTL8-V1:
                                           (SEQ ID NO: 14)
MPVPALCLLWALAMVTRPASAAPMGGPELAQHEELTLLFHGTLQLGQAL

NGVYRTTEGRLTKARNSLGLYGRTIELLGQE

ANGPTL8-V1 cDNA:
                                           (SEQ ID NO: 15)
ATGCCAGTGCCTGCTCTGTGCCTGCTCTGGGCCCTGGCAATGGTGACCC

GGCCTGCCTCAGCGGCCCCCATGGGCGGCCCAGAACTGGCACAGCATGA

GGAGCTGACCCTGCTCTTCCATGGGACCCTGCAGCTGGGCCAGGCCCTC

AACGGTGTGTACAGGACCACGGAGGGACGGCTGACAAAGGCCAGGAACA

GCCTGGGTCTCTATGGCCGCACAATAGAACTCCTGGGGCAGGAG

ANGPTL8-V2:
                                           (SEQ ID NO: 16)
MPVPALCLLWALAMVTRPASAVSRGRDAAQELRASLLETQMEEDILQLQ

AEATAEVLGEVAQAQKVLRDSVQRLEVQLRSAWLGPAYREFEVLKAHAD

KQSHILWALTGHVQRQRREMVAQQHRLRQIQERLHTAALPA

ANGPTL8-V2 cDNA:
                                           (SEQ ID NO: 17)
ATGCCAGTGCCTGCTCTGTGCCTGCTCTGGGCCCTGGCAATGGTGACCC

GGCCTGCCTCAGCGGTCAGCCGGGGCCGGGATGCAGCCCAGGAACTTCG
```

GGCAAGCCTGTTGGAGACTCAGATGGAGGAGGATATTCTGCAGCTGCAG

GCAGAGGCCACAGCTGAGGTGCTGGGGGAGGTGGCCCAGGCACAGAAGG

TGCTACGGGACAGCGTGCAGCGGCTAGAAGTCCAGCTGAGGAGCGCCTG

GCTGGGCCCTGCCTACCGAGAATTTGAGGTCTTAAAGGCTCACGCTGAC

AAGCAGAGCCACATCCTATGGGCCCTCACAGGCCACGTGCAGCGGCAGA

GGCGGGAGATGGTGGCACAGCAGCATCGGCTGCGACAGATCCAGGAGAG

ACTCCACACAGCGGCGCTCCCAGCCTGA

---

What is claimed is:

1. A method of reducing triglyceride levels in a subject having or at risk of developing elevated triglyceride levels, the method comprising:
administering to the subject a polypeptide comprising a contiguous amino acid sequence having at least 95% sequence identity to the amino acid sequence of amino acids 80-198 of full-length angiopoietin-like protein 8 (ANGPTL8) (SEQ ID NO. 1),
wherein the polypeptide lacks the amino acids 21-70 of full-length ANGPTL8 (SEQ ID NO: 1), and
wherein the polypeptide is administered in an amount effective to reduce the triglyceride levels in the subject.

2. The method of claim 1, wherein the contiguous amino acid sequence has at least 97% sequence identity to the amino acid sequence of amino acids 80-198 of full-length ANGPTL8 (SEQ ID NO. 1).

3. The method of claim 1, wherein the contiguous amino acid sequence has at least 99% sequence identity to the amino acid sequence of amino acids 80-198 of full-length ANGPTL8 (SEQ ID NO. 1).

4. The method of claim 1, wherein the contiguous amino acid sequence has the amino acid sequence of amino acids 80-198 of full-length ANGPTL8 (SEQ ID NO. 1).

5. The method of claim 4, wherein the subject has elevated triglyceride levels.

6. The method of claim 5, wherein the subject is overweight or obese.

7. The method of claim 1, wherein a heterologous polypeptide is conjugated to the N-terminus or C-terminus of the polypeptide.

8. The method of claim 7, wherein the heterologous polypeptide is albumin or human serum albumin.

9. The method of claim 7, wherein the heterologous polypeptide is conjugated to the polypeptide via a cleavable linker sequence or a non-cleavable linker sequence.

10. The method of claim 7, wherein the heterologous polypeptide is an immunoglobulin Fc.

11. The method of claim 1, wherein the administering reduces triglyceride levels by at least 5% compared to triglyceride levels in the subject prior to the administering of the polypeptide.

12. The method of claim 1, wherein the administering reduces triglyceride levels by at least 10% compared to triglyceride levels in the subject prior to the administering of the polypeptide.

13. The method of claim 1, wherein the administering reduces triglyceride levels by at least 20% compared to triglyceride levels in the subject prior to the administering of the polypeptide.

14. The method of claim 1, wherein the subject is overweight or obese.

15. The method of claim 1, wherein the subject has diabetes.

16. The method of claim 1, wherein the subject has hypothyroidism.

17. The method of claim 1, wherein the subject has elevated triglyceride levels.

18. The method of claim 17, wherein an immunoglobulin Fc is conjugated to the N-terminus or C-terminus of the polypeptide.

19. The method of claim 5, wherein an immunoglobulin Fc is conjugated to the N-terminus or C-terminus of the polypeptide.

20. The method of claim 6, wherein an immunoglobulin Fc is conjugated to the N-terminus or C-terminus of the polypeptide.

\* \* \* \* \*

SEQUENCE LISTING

<160> NUMBER OF SEQ ID NOS: 32

<210> SEQ ID NO 1
<211> LENGTH: 198
<212> TYPE: PRT
<213> ORGANISM: Homo sapiens

<400> SEQUENCE: 1

```
Met Pro Val Pro Ala Leu Cys Leu Leu Trp Ala Leu Ala Met Val Thr
1               5                   10                  15

Arg Pro Ala Ser Ala Ala Pro Met Gly Gly Pro Glu Leu Ala Gln His
            20                  25                  30

Glu Glu Leu Thr Leu Leu Phe His Gly Thr Leu Gln Leu Gly Gln Ala
        35                  40                  45

Leu Asn Gly Val Tyr Arg Thr Thr Glu Gly Arg Leu Thr Lys Ala Arg
    50                  55                  60

Asn Ser Leu Gly Leu Tyr Gly Arg Thr Ile Glu Leu Leu Gly Gln Glu
65                  70                  75                  80

Val Ser Arg Gly Arg Asp Ala Ala Gln Glu Leu Arg Ala Ser Leu Leu
                85                  90                  95

Glu Thr Gln Met Glu Glu Asp Ile Leu Gln Leu Gln Ala Glu Ala Thr
            100                 105                 110

Ala Glu Val Leu Gly Glu Val Ala Gln Ala Gln Lys Val Leu Arg Asp
        115                 120                 125

Ser Val Gln Arg Leu Glu Val Gln Leu Arg Ser Ala Trp Leu Gly Pro
    130                 135                 140

Ala Tyr Arg Glu Phe Glu Val Leu Lys Ala His Ala Asp Lys Gln Ser
145                 150                 155                 160

His Ile Leu Trp Ala Leu Thr Gly His Val Gln Arg Gln Arg Arg Glu
                165                 170                 175

Met Val Ala Gln Gln His Arg Leu Arg Gln Ile Gln Glu Arg Leu His
            180                 185                 190

Thr Ala Ala Leu Pro Ala
        195
```

<210> SEQ ID NO 2
<211> LENGTH: 2325
<212> TYPE: DNA
<213> ORGANISM: Homo sapiens

<400> SEQUENCE: 2

```
ataccttaga ccctcagtca tgccagtgcc tgctctgtgc ctgctctggg ccctggcaat      60
ggtgacccgg cctgcctcag cggcccccat gggcggccca gaactggcac agcatgagga     120
gctgaccctg ctcttccatg ggaccctgca gctgggccag gccctcaacg gtgtgtacag     180
gaccacggag gaacggctga caaaggccag gaacagcctg ggtctctatg gccgcacaat     240
agaactcctg gggcaggagg tcagccgggg ccgggatgca gcccaggaac ttcgggcaag     300
cctgttggag actcaggtgg gcaccgtagc tgcgacactg tggggtggcc aggagtccaa     360
```

| | |
|---|---|
| agaggagttc gtgtctaggg taaccaacca tcctggtttg cccaggactg aagggattcc | 420 |
| tgggatacaa gattttcagc gataaactca ggcaagtcct taggtacaca agatgagtt | 480 |
| ggacatccta ctagtgaccc actgtttatt aagcagatgg aggaggatat tctgcagctg | 540 |
| caggcagagg ccacagctga ggtgctgggg gaggtggccc aggcacagaa ggtgctacgg | 600 |
| gacagcgtgc agcggctaga agtccagctg aggagcgcct ggctgggccc tgcctaccga | 660 |
| gaatttgagg tcttaaaggt aaggagctcc cccaaccta gtgggctgag accctgattt | 720 |
| ccggccagaa ctcgcttctg caccttgagt cccaaagacc tcccagatca gcctcccagc | 780 |
| tctgtggcct ctaccctgca gtccccagca caaaactcaa gtccttttgt gtgcctcagt | 840 |
| ttcccttttg tgtgcctcag ttgcaaataa gggcaacacc tgatatctca cagtagggcc | 900 |
| aggtactcaa tgcaggtaaa atattcagca tggggcgggc acacagttgg tgctcaataa | 960 |
| attctttttt tttttttttt tgagacagag tctcactgtt gcccaggctg gagtgcagtg | 1020 |
| gtgtgatctt ggctcactgc aacctccacc tcctaggttc aagtgattct cctgcctcag | 1080 |
| cctcctgagt agctggaatt acaggtgcac cagctaattt ttgtattttt tagtagagat | 1140 |
| gggatttcac catgttggcc aggctggtct cgaactcctg acctcaaggg atctgcctgc | 1200 |
| ctcggtttcc caaagtgctg ggattacagg tgtgagccac tacacctggc caataaattc | 1260 |
| ttactactag agaaactggt aacattttgt gagcacccag taagtaccca gcactgttct | 1320 |
| atgcccttta ataatccata tgatggccgg gcatggtggc tcatgcctgt aatcccagca | 1380 |
| ctttgggtag ctaaggtggg tggaacactt aaggtcagga gttcgagacc acctggcca | 1440 |
| acatggtgaa accccgtctc tactaaaaat acaaaaaatt agctgggcgt ggtggcacat | 1500 |
| gcctgtagtc ccagctactc aggaggctta ggtaggagaa tcgcttgaac ctgggaggtg | 1560 |
| gaggttgcag tgagctgaga tcgtgtcatt gcactcagcc tgggtgacag agagagactc | 1620 |
| aaaaaaaaaa aaaatccat aggatgttca tcacctcccc atgaagtgag tcctatttta | 1680 |
| tccccatttt acagatgggg aaactgaggc caaagagcat tgttgacttg ctgggtcaca | 1740 |
| cagatacaat gaggggctgg ggcagagggt caggggatgg gaggtgaggt ggctgtcggc | 1800 |
| tgaggtttcc attctgaccc ccacaggctc acgctgacaa gcagagccac atcctatggg | 1860 |
| ccctcacagg ccacgtgcag cggcagaggc gggagatggt ggcacagcag catcggctgc | 1920 |
| gacagatcca ggagaggtga gcctggcagg ggtttggcag gcagggcagt tggatggggg | 1980 |
| gcgcacaggg cagctggaaa ggggccccct cacctgggct gagccacatc tccctcccca | 2040 |
| gactccacac agcggcgctc ccagcctgaa tctgcctgga tggaactgag gaccaatcat | 2100 |
| gctgcaagga acacttccac gccccgtgag gcccctgtgc agggaggagc tgcctgttca | 2160 |
| ctgggatcag ccagggcgcc gggcccccact tctgagcaca gagcagagac agacgcaggc | 2220 |
| ggggacaaag gcagaggatg tagccccatt ggggaggggt ggaggaagga catgtaccct | 2280 |
| ttcatgccta cacacccctc attaaagcag agtcgtggca tctca | 2325 |

<210> SEQ ID NO 3
<211> LENGTH: 755
<212> TYPE: RNA
<213> ORGANISM: Homo sapiens

<400> SEQUENCE: 3

| | |
|---|---|
| aaccagaccc cagcagccag gccgccggcc gccgggcccg gcaagggacc cggccgccca | 60 |
| gcggccccca gggcggccca gaacggcaca gcagaggagc gacccgcccc agggacccgc | 120 |

```
agcgggccag gccccaacgg ggacaggacc acggagggac ggcgacaaag gccaggaaca        180
gccgggccag gccgcacaaa gaacccgggg caggaggcag ccggggccgg gagcagccca        240
ggaaccgggc aagccgggag accagaggag gaggaacgca gcgcaggcag aggccacagc        300
gagggcgggg gaggggccca ggcacagaag ggcacgggac agcggcagcg gcagaagcca        360
gcgaggagcg ccggcgggcc cgccaccgag aagaggcaaa ggccacgcga caagcagagc        420
cacaccaggg ccccacaggc cacggcagcg gcagaggcgg gagaggggca cagcagcacg        480
gcgcgacaga ccaggagaga cccacacagc ggcgccccag ccgaacgccg gaggaacgag        540
gaccaacagc gcaaggaaca cccacgcccc ggaggccccg gcaggaggga gcgccgcacg        600
ggacagccag ggcgccgggc cccaccgagc acagagcaga gacagacgca ggcggggaca        660
aaggcagagg agagccccag gggaggggggg aggaaggaca gacccccagcc acacacccccc        720 aaaagcagag cgggcaccaa aaaaaaaaaa aaaaa                                   755

<210> SEQ ID NO 4
<211> LENGTH: 597
<212> TYPE: DNA
<213> ORGANISM: Artificial sequence
<220> FEATURE:
<223> OTHER INFORMATION: Synthetic nucleic acid sequence

<400> SEQUENCE: 4
atgccagtgc ctgctctgtg cctgctctgg gccctggcaa tggtgacccg gcctgcctca         60
gcggccccca tgggcggccc agaactggca cagcatgagg agctgaccct gctcttccat        120
gggaccctgc agctgggcca ggccctcaac ggtgtgtaca ggaccacgga gggacggctg        180
acaaaggcca ggaacagcct gggtctctat ggccgcacaa tagaactcct ggggcaggag        240
gtcagccggg gccgggatgc agcccaggaa cttcggggcaa gcctgttgga gactcagatg        300
gaggaggata ttctgcagct gcaggcagag gccacagctg aggtgctggg ggaggtggcc        360
caggcacaga aggtgctacg ggacagcgtg cagcggctag aagtccagct gaggagcgcc        420
tggctgggcc ctgcctaccg agaatttgag gtcttaaagg ctcacgctga caagcagagc        480
cacatcctat gggccctcac aggccacgtg cagcggcaga ggcgggagat ggtggcacag        540
cagcatcggc tgcgacagat ccaggagaga ctccacacag cggcgctccc agcctga           597

<210> SEQ ID NO 5
<211> LENGTH: 122
<212> TYPE: PRT
<213> ORGANISM: Artificial sequence
<220> FEATURE:
<223> OTHER INFORMATION: Synthetic polypeptide sequence

<400> SEQUENCE: 5

Leu Gly Gln Glu Val Ser Arg Gly Arg Asp Ala Ala Gln Glu Leu Arg
1               5                   10                  15

Ala Ser Leu Leu Glu Thr Gln Met Glu Glu Asp Ile Leu Gln Leu Gln
            20                  25                  30

Ala Glu Ala Thr Ala Glu Val Leu Gly Glu Val Ala Gln Ala Gln Lys
        35                  40                  45

Val Leu Arg Asp Ser Val Gln Arg Leu Glu Val Gln Leu Arg Ser Ala
    50                  55                  60

Trp Leu Gly Pro Ala Tyr Arg Glu Phe Glu Val Leu Lys Ala His Ala
65                  70                  75                  80

Asp Lys Gln Ser His Ile Leu Trp Ala Leu Thr Gly His Val Gln Arg
                85                  90                  95
```

Gln Arg Arg Glu Met Val Ala Gln Gln His Arg Leu Arg Gln Ile Gln
                100                 105                 110

Glu Arg Leu His Thr Ala Ala Leu Pro Ala
        115                 120

<210> SEQ ID NO 6
<211> LENGTH: 198
<212> TYPE: PRT
<213> ORGANISM: Mus musculus

<400> SEQUENCE: 6

Met Ala Val Leu Ala Leu Cys Leu Leu Trp Thr Leu Ala Ser Ala Val
1               5                   10                  15

Arg Pro Ala Pro Val Ala Pro Leu Gly Gly Pro Glu Pro Ala Gln Tyr
            20                  25                  30

Glu Glu Leu Thr Leu Leu Phe His Gly Ala Leu Gln Leu Gly Gln Ala
        35                  40                  45

Leu Asn Gly Val Tyr Arg Ala Thr Glu Ala Arg Leu Thr Glu Ala Gly
    50                  55                  60

His Ser Leu Gly Leu Tyr Asp Arg Ala Leu Glu Phe Leu Gly Thr Glu
65                  70                  75                  80

Val Arg Gln Gly Gln Asp Ala Thr Gln Glu Leu Arg Thr Ser Leu Ser
                85                  90                  95

Glu Ile Gln Val Glu Glu Asp Ala Leu His Leu Arg Ala Glu Ala Thr
            100                 105                 110

Ala Arg Ser Leu Gly Glu Val Ala Arg Ala Gln Gln Ala Leu Arg Asp
        115                 120                 125

Thr Val Arg Arg Leu Gln Val Gln Leu Arg Gly Ala Trp Leu Gly Gln
    130                 135                 140

Ala His Gln Glu Phe Glu Thr Leu Lys Ala Arg Ala Asp Lys Gln Ser
145                 150                 155                 160

His Leu Leu Trp Ala Leu Thr Gly His Val Gln Arg Gln Gln Arg Glu
                165                 170                 175

Met Ala Glu Gln Gln Gln Trp Leu Arg Gln Ile Gln Gln Arg Leu His
            180                 185                 190

Thr Ala Ala Leu Pro Ala
        195

<210> SEQ ID NO 7
<211> LENGTH: 122
<212> TYPE: PRT
<213> ORGANISM: Artificial sequence
<220> FEATURE:
<223> OTHER INFORMATION: Synthetic polypeptide sequence

<400> SEQUENCE: 7

Leu Gly Thr Glu Val Arg Gln Gly Gln Asp Ala Thr Gln Glu Leu Arg
1               5                   10                  15

Thr Ser Leu Ser Glu Ile Gln Val Glu Glu Asp Ala Leu His Leu Arg
            20                  25                  30

Ala Glu Ala Thr Ala Arg Ser Leu Gly Glu Val Ala Arg Ala Gln Gln
        35                  40                  45

Ala Leu Arg Asp Thr Val Arg Arg Leu Gln Val Gln Leu Arg Gly Ala
    50                  55                  60

Trp Leu Gly Gln Ala His Gln Glu Phe Glu Thr Leu Lys Ala Arg Ala
65                  70                  75                  80

-continued

Asp Lys Gln Ser His Leu Leu Trp Ala Leu Thr Gly His Val Gln Arg
            85                  90                  95

Gln Gln Arg Glu Met Ala Glu Gln Gln Trp Leu Arg Gln Ile Gln
            100                 105                 110

Gln Arg Leu His Thr Ala Ala Leu Pro Ala
        115                 120

<210> SEQ ID NO 8
<211> LENGTH: 493
<212> TYPE: PRT
<213> ORGANISM: Homo sapiens

<400> SEQUENCE: 8

Met Arg Pro Leu Cys Val Thr Cys Trp Trp Leu Gly Leu Leu Ala Ala
1               5                   10                  15

Met Gly Ala Val Ala Gly Gln Glu Asp Gly Phe Glu Gly Thr Glu Glu
            20                  25                  30

Gly Ser Pro Arg Glu Phe Ile Tyr Leu Asn Arg Tyr Lys Arg Ala Gly
        35                  40                  45

Glu Ser Gln Asp Lys Cys Thr Tyr Thr Phe Ile Val Pro Gln Gln Arg
    50                  55                  60

Val Thr Gly Ala Ile Cys Val Asn Ser Lys Glu Pro Glu Val Leu Leu
65                  70                  75                  80

Glu Asn Arg Val His Lys Gln Glu Leu Glu Leu Leu Asn Asn Glu Leu
            85                  90                  95

Leu Lys Gln Lys Arg Gln Ile Glu Thr Leu Gln Gln Leu Val Glu Val
            100                 105                 110

Asp Gly Gly Ile Val Ser Glu Val Lys Leu Leu Arg Lys Glu Ser Arg
        115                 120                 125

Asn Met Asn Ser Arg Val Thr Gln Leu Tyr Met Gln Leu Leu His Glu
    130                 135                 140

Ile Ile Arg Lys Arg Asp Asn Ala Leu Glu Leu Ser Gln Leu Glu Asn
145                 150                 155                 160

Arg Ile Leu Asn Gln Thr Ala Asp Met Leu Gln Leu Ala Ser Lys Tyr
            165                 170                 175

Lys Asp Leu Glu His Lys Tyr Gln His Leu Ala Thr Leu Ala His Asn
            180                 185                 190

Gln Ser Glu Ile Ile Ala Gln Leu Glu Glu His Cys Gln Arg Val Pro
        195                 200                 205

Ser Ala Arg Pro Val Pro Gln Pro Pro Ala Ala Pro Pro Arg Val
    210                 215                 220

Tyr Gln Pro Pro Thr Tyr Asn Arg Ile Ile Asn Gln Ile Ser Thr Asn
225                 230                 235                 240

Glu Ile Gln Ser Asp Gln Asn Leu Lys Val Leu Pro Pro Pro Leu Pro
            245                 250                 255

Thr Met Pro Thr Leu Thr Ser Leu Pro Ser Ser Thr Asp Lys Pro Ser
            260                 265                 270

Gly Pro Trp Arg Asp Cys Leu Gln Ala Leu Glu Asp Gly His Asp Thr
        275                 280                 285

Ser Ser Ile Tyr Leu Val Lys Pro Glu Asn Thr Asn Arg Leu Met Gln
    290                 295                 300

Val Trp Cys Asp Gln Arg His Asp Pro Gly Gly Trp Thr Val Ile Gln
305                 310                 315                 320

Arg Arg Leu Asp Gly Ser Val Asn Phe Phe Arg Asn Trp Glu Thr Tyr
            325                 330                 335

```
Lys Gln Gly Phe Gly Asn Ile Asp Gly Glu Tyr Trp Leu Gly Leu Glu
            340                 345                 350

Asn Ile Tyr Trp Leu Thr Asn Gln Gly Asn Tyr Lys Leu Leu Val Thr
            355                 360                 365

Met Glu Asp Trp Ser Gly Arg Lys Val Phe Ala Glu Tyr Ala Ser Phe
            370                 375                 380

Arg Leu Glu Pro Glu Ser Glu Tyr Tyr Lys Leu Arg Leu Gly Arg Tyr
385                 390                 395                 400

His Gly Asn Ala Gly Asp Ser Phe Thr Trp His Asn Gly Lys Gln Phe
                405                 410                 415

Thr Thr Leu Asp Arg Asp His Asp Val Tyr Thr Gly Asn Cys Ala His
            420                 425                 430

Tyr Gln Lys Gly Gly Trp Trp Tyr Asn Ala Cys Ala His Ser Asn Leu
            435                 440                 445

Asn Gly Val Trp Tyr Arg Gly Gly His Tyr Arg Ser Arg Tyr Gln Asp
            450                 455                 460

Gly Val Tyr Trp Ala Glu Phe Arg Gly Gly Ser Tyr Ser Leu Lys Lys
465                 470                 475                 480

Val Val Met Met Ile Arg Pro Asn Pro Asn Thr Phe His
                485                 490

<210> SEQ ID NO 9
<211> LENGTH: 119
<212> TYPE: PRT
<213> ORGANISM: Artificial sequence
<220> FEATURE:
<223> OTHER INFORMATION: Synthetic polypeptide sequence

<400> SEQUENCE: 9

Leu Glu Asn Arg Val His Lys Gln Glu Leu Glu Leu Leu Asn Asn Glu
1               5                   10                  15

Leu Leu Lys Gln Lys Arg Gln Ile Glu Thr Leu Gln Gln Leu Val Glu
            20                  25                  30

Val Asp Gly Gly Ile Val Ser Glu Val Lys Leu Leu Arg Lys Glu Ser
        35                  40                  45

Arg Asn Met Asn Ser Arg Val Thr Gln Leu Tyr Met Gln Leu Leu His
    50                  55                  60

Glu Ile Ile Arg Lys Arg Asp Asn Ala Leu Glu Leu Ser Gln Leu Glu
65                  70                  75                  80

Asn Arg Ile Leu Asn Gln Thr Ala Asp Met Leu Gln Leu Ala Ser Lys
                85                  90                  95

Tyr Lys Asp Leu Glu His Lys Tyr Gln His Leu Ala Thr Leu Ala His
            100                 105                 110

Asn Gln Ser Glu Ile Ile Ala
        115

<210> SEQ ID NO 10
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 10
tacatatcta gaatgccagt gcctgctctg tg                                       32

<210> SEQ ID NO 11
```

<210> SEQ ID NO 11
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 11
cgcggatcct caggctggga gcgccgc                                               27

<210> SEQ ID NO 12
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 12
tacatatcta gaatgccagt gcctgctctg tg                                         32

<210> SEQ ID NO 13
<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 13
cgcggatcct cactcctgcc ccaggagttc                                            30

<210> SEQ ID NO 14
<211> LENGTH: 80
<212> TYPE: PRT
<213> ORGANISM: Artificial sequence
<220> FEATURE:
<223> OTHER INFORMATION: Synthetic polypeptide sequence

<400> SEQUENCE: 14

Met Pro Val Pro Ala Leu Cys Leu Leu Trp Ala Leu Ala Met Val Thr
1               5                   10                  15

Arg Pro Ala Ser Ala Ala Pro Met Gly Gly Pro Glu Leu Ala Gln His
            20                  25                  30

Glu Glu Leu Thr Leu Leu Phe His Gly Thr Leu Gln Leu Gly Gln Ala
        35                  40                  45

Leu Asn Gly Val Tyr Arg Thr Thr Glu Gly Arg Leu Thr Lys Ala Arg
    50                  55                  60

Asn Ser Leu Gly Leu Tyr Gly Arg Thr Ile Glu Leu Leu Gly Gln Glu
65                  70                  75                  80

<210> SEQ ID NO 15
<211> LENGTH: 240
<212> TYPE: DNA
<213> ORGANISM: Artificial sequence
<220> FEATURE:
<223> OTHER INFORMATION: Synthetic nucleic acid sequence

<400> SEQUENCE: 15
atgccagtgc ctgctctgtg cctgctctgg gccctggcaa tggtgacccg gcctgcctca          60
gcggccccca tgggcggccc agaactggca cagcatgagg agctgaccct gctcttccat         120
gggaccctgc agctgggcca ggccctcaac ggtgtgtaca ggaccacgga gggacggctg         180
acaaaggcca ggaacagcct gggtctctat ggccgcacaa tagaactcct ggggcaggag         240

<210> SEQ ID NO 16

```
<211> LENGTH: 139
<212> TYPE: PRT
<213> ORGANISM: Artificial sequence
<220> FEATURE:
<223> OTHER INFORMATION: Synthetic polypeptide sequence

<400> SEQUENCE: 16

Met Pro Val Pro Ala Leu Cys Leu Leu Trp Ala Leu Ala Met Val Thr
1               5                   10                  15

Arg Pro Ala Ser Ala Val Ser Arg Gly Arg Asp Ala Ala Gln Glu Leu
            20                  25                  30

Arg Ala Ser Leu Leu Glu Thr Gln Met Glu Glu Asp Ile Leu Gln Leu
        35                  40                  45

Gln Ala Glu Ala Thr Ala Glu Val Leu Gly Glu Val Ala Gln Ala Gln
    50                  55                  60

Lys Val Leu Arg Asp Ser Val Gln Arg Leu Glu Val Gln Leu Arg Ser
65                  70                  75                  80

Ala Trp Leu Gly Pro Ala Tyr Arg Glu Phe Glu Val Leu Lys Ala His
                85                  90                  95

Ala Asp Lys Gln Ser His Ile Leu Trp Ala Leu Thr Gly His Val Gln
            100                 105                 110

Arg Gln Arg Arg Glu Met Val Ala Gln Gln His Arg Leu Arg Gln Ile
        115                 120                 125

Gln Glu Arg Leu His Thr Ala Ala Leu Pro Ala
    130                 135

<210> SEQ ID NO 17
<211> LENGTH: 420
<212> TYPE: DNA
<213> ORGANISM: Artificial sequence
<220> FEATURE:
<223> OTHER INFORMATION: Synthetic nucleic acid sequence

<400> SEQUENCE: 17
atgccagtgc ctgctctgtg cctgctctgg gccctggcaa tggtgacccg gcctgcctca      60
gcggtcagcc ggggccggga tgcagcccag gaacttcggg caagcctgtt ggagactcag     120
atggaggagg atattctgca gctgcaggca gaggccacac tgaggtgctg ggggagtgt      180 gcccaggcac agaaggtgct acgggacagc gtgcagcggc tagaagtcca gctgaggagc     240
gcctggctgg ccctgcctac cgagaatttt gaggtcttaa aggctcacgc tgacaagcag     300
agccacatcc tatgggccct cacaggccac gtgcagcggc agaggcggga gatggtggca     360
cagcagcatc ggctgcgaca gatccaggag agactccaca cagcggcgct cccagcctga     420

<210> SEQ ID NO 18
<211> LENGTH: 5
<212> TYPE: PRT
<213> ORGANISM: Artificial sequence
<220> FEATURE:
<223> OTHER INFORMATION: Synthetic polypeptide sequence
<220> FEATURE:
<221> NAME/KEY: MISC_FEATURE
<222> LOCATION: (1)..(5)
<223> OTHER INFORMATION: this stretch of nucleotides may be repeated up
      to 50 times

<400> SEQUENCE: 18

Gly Ser Gly Gly Ser
1               5

<210> SEQ ID NO 19
```

```
<211> LENGTH: 5
<212> TYPE: PRT
<213> ORGANISM: Artificial sequence
<220> FEATURE:
<223> OTHER INFORMATION: Synthetic polypeptide sequence
<220> FEATURE:
<221> NAME/KEY: MISC_FEATURE
<222> LOCATION: (1)..(1)
<223> OTHER INFORMATION: this residue may be repeated up to 20 times
<220> FEATURE:
<221> NAME/KEY: MISC_FEATURE
<222> LOCATION: (1)..(5)
<223> OTHER INFORMATION: this stretch of nucleotides may be repeated up
      to 20 times
<220> FEATURE:
<221> NAME/KEY: MISC_FEATURE
<222> LOCATION: (2)..(2)
<223> OTHER INFORMATION: this residue may be repeated up to 20 times
<220> FEATURE:
<221> NAME/KEY: MISC_FEATURE
<222> LOCATION: (3)..(3)
<223> OTHER INFORMATION: this residue may be repeated up to 20 times
<220> FEATURE:
<221> NAME/KEY: MISC_FEATURE
<222> LOCATION: (4)..(4)
<223> OTHER INFORMATION: this residue may be repeated up to 20 times
<220> FEATURE:
<221> NAME/KEY: MISC_FEATURE
<222> LOCATION: (5)..(5)
<223> OTHER INFORMATION: this residue may be repeated up to 20 times

<400> SEQUENCE: 19

Gly Ser Gly Ser Gly
1               5

<210> SEQ ID NO 20
<211> LENGTH: 5
<212> TYPE: PRT
<213> ORGANISM: Artificial sequence
<220> FEATURE:
<223> OTHER INFORMATION: Synthetic polypeptide sequence
<220> FEATURE:
<221> NAME/KEY: MISC_FEATURE
<222> LOCATION: (1)..(5)
<223> OTHER INFORMATION: this stretch of nucleotides may be repeated up
      to 20 times
<220> FEATURE:
<221> NAME/KEY: MISC_FEATURE
<222> LOCATION: (5)..(5)
<223> OTHER INFORMATION: this residue may be repeated up to 20 times

<400> SEQUENCE: 20

Gly Ser Gly Gly Ser
1               5

<210> SEQ ID NO 21
<211> LENGTH: 5
<212> TYPE: PRT
<213> ORGANISM: Artificial sequence
<220> FEATURE:
<223> OTHER INFORMATION: Synthetic polypeptide sequence
<220> FEATURE:
<221> NAME/KEY: MISC_FEATURE
<222> LOCATION: (1)..(5)
<223> OTHER INFORMATION: this stretch of nucleotides may be repeated up
      to 20 times
<220> FEATURE:
<221> NAME/KEY: MISC_FEATURE
<222> LOCATION: (4)..(4)
<223> OTHER INFORMATION: this residue may be repeated up to 20 times

<400> SEQUENCE: 21

Gly Ser Gly Ser Gly
1               5
```

```
<210> SEQ ID NO 22
<211> LENGTH: 4
<212> TYPE: PRT
<213> ORGANISM: Artificial sequence
<220> FEATURE:
<223> OTHER INFORMATION: Synthetic polypeptide sequence
<220> FEATURE:
<221> NAME/KEY: MISC_FEATURE
<222> LOCATION: (1)..(4)
<223> OTHER INFORMATION: this stretch of nucleotides may be repeated up
      to 20 times
<220> FEATURE:
<221> NAME/KEY: MISC_FEATURE
<222> LOCATION: (4)..(4)
<223> OTHER INFORMATION: this residue may be repeated up to 20 times

<400> SEQUENCE: 22

Gly Gly Gly Ser
1

<210> SEQ ID NO 23
<211> LENGTH: 4
<212> TYPE: PRT
<213> ORGANISM: Artificial sequence
<220> FEATURE:
<223> OTHER INFORMATION: Synthetic polypeptide sequence

<400> SEQUENCE: 23

Gly Gly Ser Gly
1

<210> SEQ ID NO 24
<211> LENGTH: 5
<212> TYPE: PRT
<213> ORGANISM: Artificial sequence
<220> FEATURE:
<223> OTHER INFORMATION: Synthetic polypeptide sequence

<400> SEQUENCE: 24

Gly Gly Ser Gly Gly
1               5

<210> SEQ ID NO 25
<211> LENGTH: 5
<212> TYPE: PRT
<213> ORGANISM: Artificial sequence
<220> FEATURE:
<223> OTHER INFORMATION: Synthetic polypeptide sequence

<400> SEQUENCE: 25

Gly Ser Gly Ser Gly
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic polypeptide sequence

<400> SEQUENCE: 26

Gly Ser Gly Gly Gly
1               5

<210> SEQ ID NO 27
<211> LENGTH: 5
<212> TYPE: PRT
```

```
<213> ORGANISM: Artificial sequence
<220> FEATURE:
<223> OTHER INFORMATION: Synthetic polypeptide sequence

<400> SEQUENCE: 27

Gly Gly Gly Ser Gly
1               5

<210> SEQ ID NO 28
<211> LENGTH: 5
<212> TYPE: PRT
<213> ORGANISM: Artificial sequence
<220> FEATURE:
<223> OTHER INFORMATION: Synthetic polypeptide sequence

<400> SEQUENCE: 28

Gly Ser Ser Ser Gly
1               5

<210> SEQ ID NO 29
<211> LENGTH: 4
<212> TYPE: PRT
<213> ORGANISM: Artificial sequence
<220> FEATURE:
<223> OTHER INFORMATION: Synthetic polypeptide sequence
<220> FEATURE:
<221> NAME/KEY: MISC_FEATURE
<222> LOCATION: (1)..(4)
<223> OTHER INFORMATION: this stretch of nucleotides may be repeated up
      to 50 times

<400> SEQUENCE: 29

Gly Gly Gly Ser
1

<210> SEQ ID NO 30
<211> LENGTH: 5
<212> TYPE: PRT
<213> ORGANISM: Artificial sequence
<220> FEATURE:
<223> OTHER INFORMATION: Synthetic polypeptide sequence
<220> FEATURE:
<221> NAME/KEY: MISC_FEATURE
<222> LOCATION: (1)..(5)
<223> OTHER INFORMATION: this stretch of nucleotides may be repeated up
      to 50 times

<400> SEQUENCE: 30

Gly Gly Gly Gly Ser
1               5

<210> SEQ ID NO 31
<211> LENGTH: 4
<212> TYPE: PRT
<213> ORGANISM: Artificial sequence
<220> FEATURE:
<223> OTHER INFORMATION: Synthetic polypeptide sequence

<400> SEQUENCE: 31

Gly Gly Gly Ser
1

<210> SEQ ID NO 32
<211> LENGTH: 5
<212> TYPE: PRT
<213> ORGANISM: Artificial sequence
<220> FEATURE:
<223> OTHER INFORMATION: Synthetic polypeptide sequence
<220> FEATURE:
```

-continued

```
<221> NAME/KEY: MISC_FEATURE
<222> LOCATION: (1)..(5)
<223> OTHER INFORMATION: this stretch of nucleotides may be repeated up
      to 50 times

<400> SEQUENCE: 32

Gly Gly Gly Gly Ser
1               5
```